US012710429B2

(12) United States Patent
Gorton et al.

(10) Patent No.: US 12,710,429 B2
(45) Date of Patent: Aug. 18, 2026

(54) COMPARING A MODELED MOLECULE FRAGMENTATION TO AN EXPERIMENTAL MOLECULE FRAGMENTATION

(71) Applicant: Waters Technologies Ireland Limited, Dublin (IE)

(72) Inventors: Matthew Gorton, Cramlington (GB); Michael Broughton, Killingworth (GB); Christopher Knowles, Eighton Banks (GB)

(73) Assignee: Waters Technologies Ireland Limited, Dublin (IE)

( * ) Notice: Subject to any disclaimer, the term of this patent is extended or adjusted under 35 U.S.C. 154(b) by 640 days.

(21) Appl. No.: 17/843,161

(22) Filed: Jun. 17, 2022

(65) Prior Publication Data

US 2022/0404371 A1 Dec. 22, 2022

Related U.S. Application Data

(60) Provisional application No. 63/212,287, filed on Jun. 18, 2021.

(51) Int. Cl.
*G01N 33/68* (2006.01)
*G16C 20/20* (2019.01)

(52) U.S. Cl.
CPC ......... *G01N 33/6848* (2013.01); *G16C 20/20* (2019.02)

(58) Field of Classification Search
CPC ............................ G01N 33/6848; G16C 20/20
See application file for complete search history.

(56) References Cited

U.S. PATENT DOCUMENTS

2009/0179147 A1 * 7/2009 Milgram ............ G01N 30/8675 250/281
2014/0045273 A1 * 2/2014 Cerda .................... G16C 20/20 422/83
2020/0243313 A1 * 7/2020 Bern ................... H01J 49/0036

FOREIGN PATENT DOCUMENTS

CN 101443664 A * 5/2009 ........... C07D 239/54
EP 3745443 A1 * 12/2020 ............. G01N 27/62
WO WO-2012012719 A2 * 1/2012 ......... G01N 33/6848

OTHER PUBLICATIONS

International Search Report and Written Opinion for International Patent Application No. PCT/IB2022/055656, mailed Sep. 12, 2022.
International Preliminary Report on Patentability for International Patent Application No. PCT/IB2022/055656, mailed Dec. 28, 2023.

* cited by examiner

*Primary Examiner* — Catherine T. Rastovski
*Assistant Examiner* — Nyla Gavia
(74) *Attorney, Agent, or Firm* — Goodwin Procter LLP

(57) ABSTRACT

Exemplary embodiments described herein provide improved techniques for matching an experimental mass spectrometry fragmentation against a known or predicted fragmentation from a library. Among other improvements, exemplary embodiments provide more accessible interfaces that are easier to interpret, thus allowing for more accurate and faster matches. They also may automatically accumulate multiple experimental results to determine whether several runs of a given sample cumulatively represent a library fragmentation pattern. Furthermore, exemplary embodiments provide simplified techniques for identifying and accounting for molecule variants.

21 Claims, 17 Drawing Sheets

FIG. 13

COMPARING A MODELED MOLECULE FRAGMENTATION TO AN EXPERIMENTAL MOLECULE FRAGMENTATION

CROSS-REFERENCE TO RELATED APPLICATIONS

This application claims the benefit of U.S. Provisional Patent Application No. 63/212,287, filed Jun. 18, 2021. The entire disclosure of which is hereby incorporated by reference.

BACKGROUND

Mass spectrometry (MS) may be used to identify the compounds that make up a sample. For example, among other applications MS can be used to identify the oligonucleotides ("oligos") that make up a DNA or RNA sample; it can also be used for a wide variety of other purposes. Because molecules fragment in predictable ways when subjected to MS, in some cases it may be possible to build a library of known fragmentation patterns to match against a fragmentation pattern observed in an experiment. The library may be built, for example, based on modeling or previous experimental results. An expert user typically interprets the results of the match based on an output on a graphical user interface in order to determine whether a set of experimental results match a fragmentation model stored in the library.

BRIEF SUMMARY

Exemplary embodiments relate to computer-implemented methods, as well as non-transitory computer-readable mediums storing instructions for performing the methods, apparatuses configured to perform the methods, etc.

In one aspect, a computer implemented method includes receiving input data representing a fragmentation of a molecule into a plurality of experimental fragments, comparing the fragmentation to a library of modeled fragmentations to identify a candidate match includes a plurality of modeled fragments, and displaying a graphical representation of the candidate match, the graphical representation includes a graphical element corresponding to each of the modeled fragments, where each graphical element is capable of being in an on state or an off state, and a respective graphical element is in the on state if the graphical element's modeled fragment matches a corresponding experimental fragment in the input data.

The molecule may be an oligonucleotide and the experimental fragments may represent monomers in the oligonucleotide.

The computer-implemented method may also include receiving second input data representing a second fragmentation of the molecule into a second plurality of experimental fragments, and aggregating at least the plurality of experimental fragments and the second plurality of experimental fragments into cumulative input data, where the respective graphical element is in the on state if the modeled fragment corresponding to the graphical element matches at least one of the corresponding experimental fragment in the input data or a second corresponding experimental fragment from the second input data.

The computer-implemented method may also include identifying a second candidate match, and displaying a graphical representation of the second candidate match aligned to a graphical representation of the candidate match.

The computer-implemented method may also include identifying that a specified experimental fragment is associated with one or more variant configurations, and modifying the graphical element corresponding to the specified experimental fragment with a variant identifier.

The computer-implemented method may also include receiving a selection of a selected graphical element in the graphical representation of the candidate match, and displaying a mass spectrum from the input data corresponding to the experimental fragment associated with the selected graphical element. Other technical features may be readily apparent to one skilled in the art from the following figures, descriptions, and claims.

In some embodiments, each graphical element may display a score representing how often the modeled fragment corresponding to the graphical element was found in the cumulative input data.

The computer-implemented method may also include receiving a selection of a selected graphical element in the graphical representation of the candidate match, and highlighting corresponding graphical elements in graphical representations of the cumulative input data.

The computer-implemented method may also include identifying that a plurality of experimental fragments are each associated with one or more variant configurations, and that at least one of the experimental fragments is in a variant state, and modifying the graphical elements corresponding to the plurality of experimental fragments associated with the variant configurations with a potential variant identifier.

The computer-implemented method may also include receiving a selection of the graphical element corresponding to the specified experimental fragment, receiving a selection of a selected variant configuration, and modifying the display of the graphical representation based on the selected variant configuration.

Other technical features will be readily apparent to one skilled in the art from the following figures, descriptions, and claims.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 13 is a flowchart depicting exemplary logic for identifying and displaying molecule variants in accordance with one embodiment.

DETAILED DESCRIPTION

Although library fragmentation can be a powerful tool for identifying unknown molecules, existing matching systems can be difficult to use. For example, due to the nature of experimentation a user is unlikely to see a perfect match between an experimental and modeled result; some mass peaks in the experiment are likely to be missing or shifted from their expected position. Because of this, users typically run a sample multiple times until they are reasonably confident that the library result matches the experimental sample.

Figure 1:
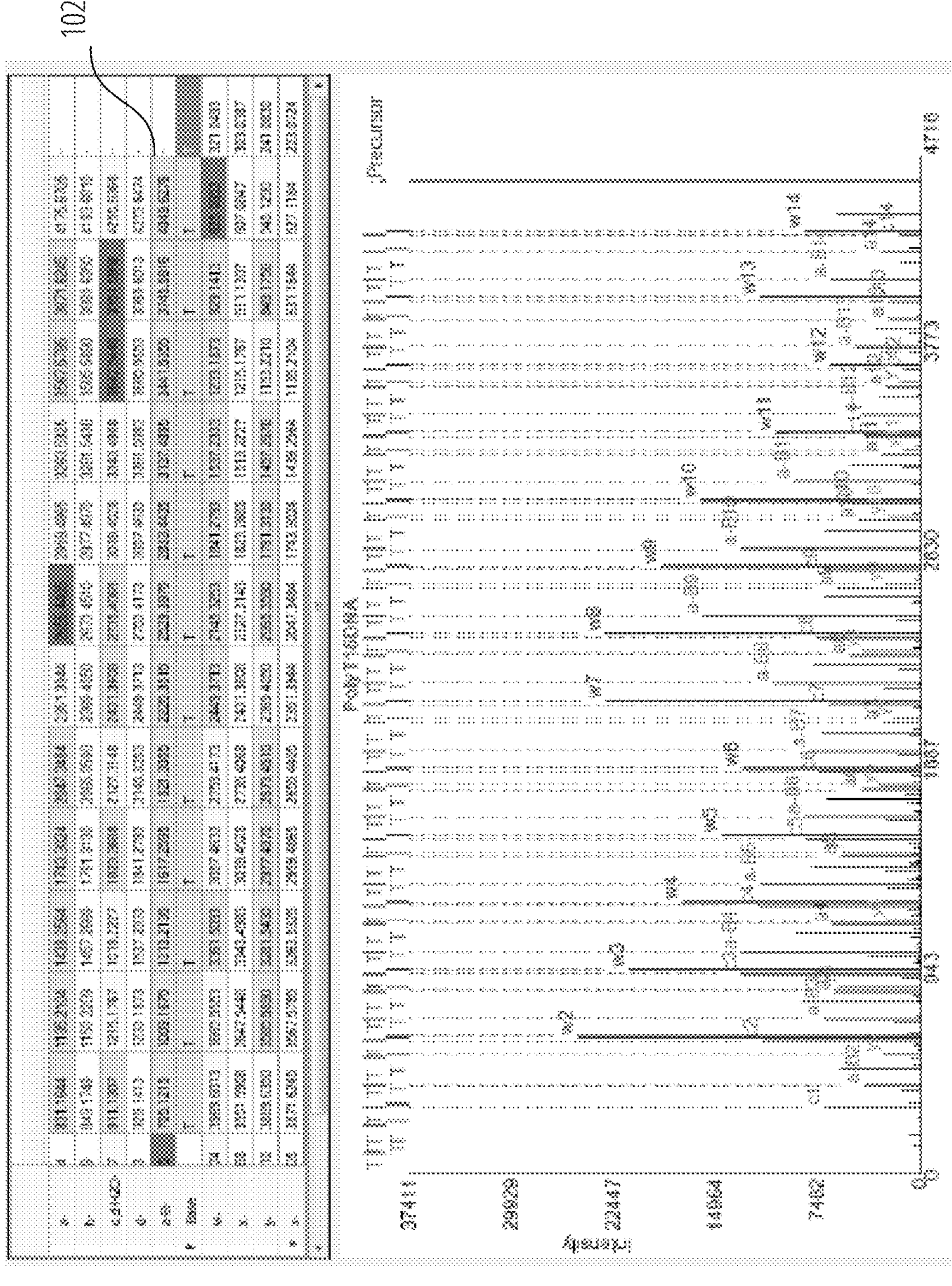
FIG. 1 depicts an exemplary graphical user interface showing a molecule fragmentation color graph.

These multiple runs can cause their own difficulties, however. Conventional systems tend to represent results as a heat map or color graph, which shows how closely each molecule of the compound matched against a given library result. FIG. 1 provides an example of a conventional user interface with a portion of a color graph 102. As can be seen, the represented compound includes many molecules (as is usually the case), and thus the output can be complex and difficult to interpret, requiring some expertise in order to judge a match. Furthermore, each experimental run is represented individually, and it can thus be difficult to determine whether the total number of runs cumulatively represent the library compound in question.

The analysis can be even more complicated due to the presence of molecule variants. For instance, when the compound being analyzed includes an oligonucleotide made up of a number of monomers, a monomer may serve as a base to which other molecules can attach. There may be a limited number of molecules that could attach to each base (e.g., about 15 variants might be able to attach to a given T-base), but there may be many such bases with possible variants in a given sample. A given variant attached to a given base may be referred to as a modification. In conventional systems, each potential modification needs to be checked individually to determine if it is an appropriate match to the experimental results.

Exemplary embodiments described herein provide improved techniques for matching an experimental fragmentation against a known fragmentation from a library. Among other improvements, exemplary embodiments provide more accessible interfaces that are easier to interpret, thus allowing for more accurate and faster matches. They also may automatically accumulate multiple experimental results to determine whether several runs of a given sample cumulatively represent a library fragmentation pattern. Furthermore, exemplary embodiments provide simplified techniques for identifying and accounting for molecule variants.

Although some embodiments are described with reference to oligonucleotide fragmentation, embodiments are not limited to this specific application. Unless a particular context is specified, it is understood that exemplary embodiments may be employed with any type of molecule fragmentation system.

Figure 2:
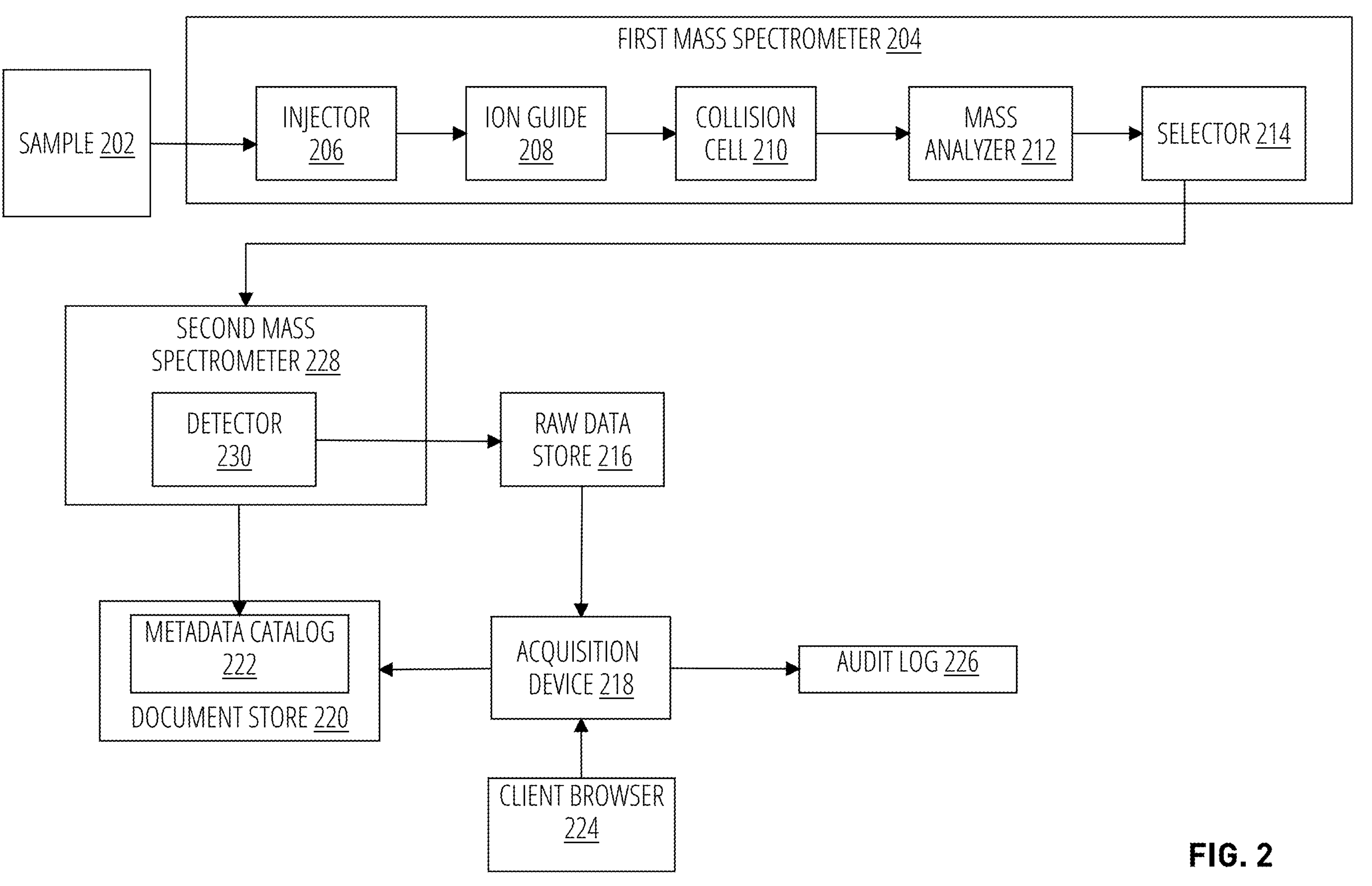
FIG. 2 illustrates an example of a mass spectrometry system according to an exemplary embodiment.

For purposes of illustration, FIG. 2 is a schematic diagram of a system that may be used in connection with techniques herein. Although FIG. 2 depicts particular types of devices in a specific tandem MS configuration, one of ordinary skill in the art will understand that different types of chromatographic devices (e.g., MS, LCMS, etc.) may also be used in connection with the present disclosure.

A sample 202 is injected into a first mass spectrometer 204 through an injector 206. Initially, the sample is desolved and ionized by a desolvation/ionization device. Desolvation can be any technique for desolvation, including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization technique. Ions resulting from the ionization are fed to a collision cell 210 by a voltage gradient being applied to an ion guide 208. Collision cell 210 can be used to pass the ions (low-energy) or to fragment the ions (high-energy). Ions may include individual elements or molecules, and may include monomers.

Different techniques (including one described in U.S. Pat. No. 6,717,130, to Bateman et al.) may be used in which an alternating voltage can be applied across the collision cell 210 to cause fragmentation. Spectra are collected for the precursors at low-energy (no collisions) and fragments at high-energy (results of collisions).

Collision cell 210 performs fragmentation of the precursor ions. Fragmentation can be used to determine the primary sequence of a peptide and subsequently lead to the identity of the originating protein. Collision cell 210 includes a gas such as helium, argon, nitrogen, air, or methane. When a charged precursor interacts with gas atoms, the resulting collisions can fragment the precursor by breaking it up into resulting fragment ions. Such fragmentation can be accomplished as using techniques described in Bateman by switching the voltage in a collision cell between a low voltage state (e.g., low energy, <5 V) which obtains MS spectra of the peptide precursor, with a high voltage state (e.g., high or elevated energy, >15V) which obtains MS spectra of the collisionally induced fragments of the precursors. High and low voltage may be referred to as high and low energy, since a high or low voltage respectively is used to impart kinetic energy to an ion.

Various protocols can be used to determine when and how to switch the voltage for such an MS/MS acquisition. For example, conventional methods trigger the voltage in either a targeted or data dependent mode (data-dependent analysis, DDA). These methods also include a coupled, gas-phase isolation (or pre-selection) of the targeted precursor. The low-energy spectra are obtained and examined by the software in real-time. When a desired mass reaches a specified intensity value in the low-energy spectrum, the voltage in the collision cell is switched to the high-energy state. The high-energy spectra are then obtained for the pre-selected precursor ion. These spectra contain fragments of the precursor peptide seen at low energy. After sufficient high-energy spectra are collected, the data acquisition reverts to low-energy in a continued search for precursor masses of suitable intensities for high-energy collisional analysis.

The output of collision cell 210 is input to a mass analyzer 212. Mass analyzer 212 can be any mass analyzer, including quadrupole, time-of-flight (TOF), ion trap, magnetic sector mass analyzers as well as combinations thereof.

A selector 214 preferentially allows ions in a predetermined mass-to-charge ratio range to pass through to a second mass spectrometer 228. Analyzing the ions using two or more mass spectrometers allows ions having very similar mass-to-charge ratios to be separated and identified; tandem MS is therefore often used in connection with the analysis of biomolecules, such as proteins and peptides.

The second mass spectrometer 228 may have a similar structure to that of the first mass spectrometer 204, and further discussion of these components is omitted here for the sake of brevity. The second mass spectrometer 228 further includes a detector 230 configured to detect ions emanating from the mass analyzer of the second mass spectrometer 228. Detector 230 can be integral with the mass analyzer 212 of the second mass spectrometer 228. For example, in the case of a TOF mass analyzer, detector 230 can be a microchannel plate detector that counts intensity of ions, i.e., counts numbers of ions impinging it.

A raw data store 216 may provide permanent storage for storing the ion counts for analysis. For example, raw data store 216 can be an internal or external computer data storage device such as a disk, flash-based storage, and the like. An acquisition device 218 analyzes the stored data. Data can also be analyzed in real time without requiring storage in a storage medium 124. In real time analysis, selector 214 passes data to be analyzed directly to computer 126 without first storing it to permanent storage.

Metadata describing various parameters related to data acquisition may be generated alongside the raw data. This information may include a configuration of the first mass spectrometer 204 or second mass spectrometer 228 (or other apparatus that acquires the data), which may define a data type. An identifier (e.g., a key) for a codec that is configured to decode the data may also be stored as part of the metadata and/or with the raw data. The metadata may be stored in a metadata catalog 222 in a document store 220.

The acquisition device 218 may operate according to a workflow, providing visualizations of data to an analyst at each of the workflow steps and allowing the analyst to generate output data by performing processing specific to the workflow step. The workflow may be generated and retrieved via a client browser 224. As the acquisition device 218 performs the steps of the workflow, it may read read raw data from a stream of data located in the raw data store 216. As the acquisition device 218 performs the steps of the workflow, it may generate processed data that is stored in a metadata catalog 222 in a document store 220; alternatively or in addition, the processed data may be stored in a different location specified by a user of the acquisition device 218. It may also generate audit records that may be stored in an audit log 226.

Figure 14:
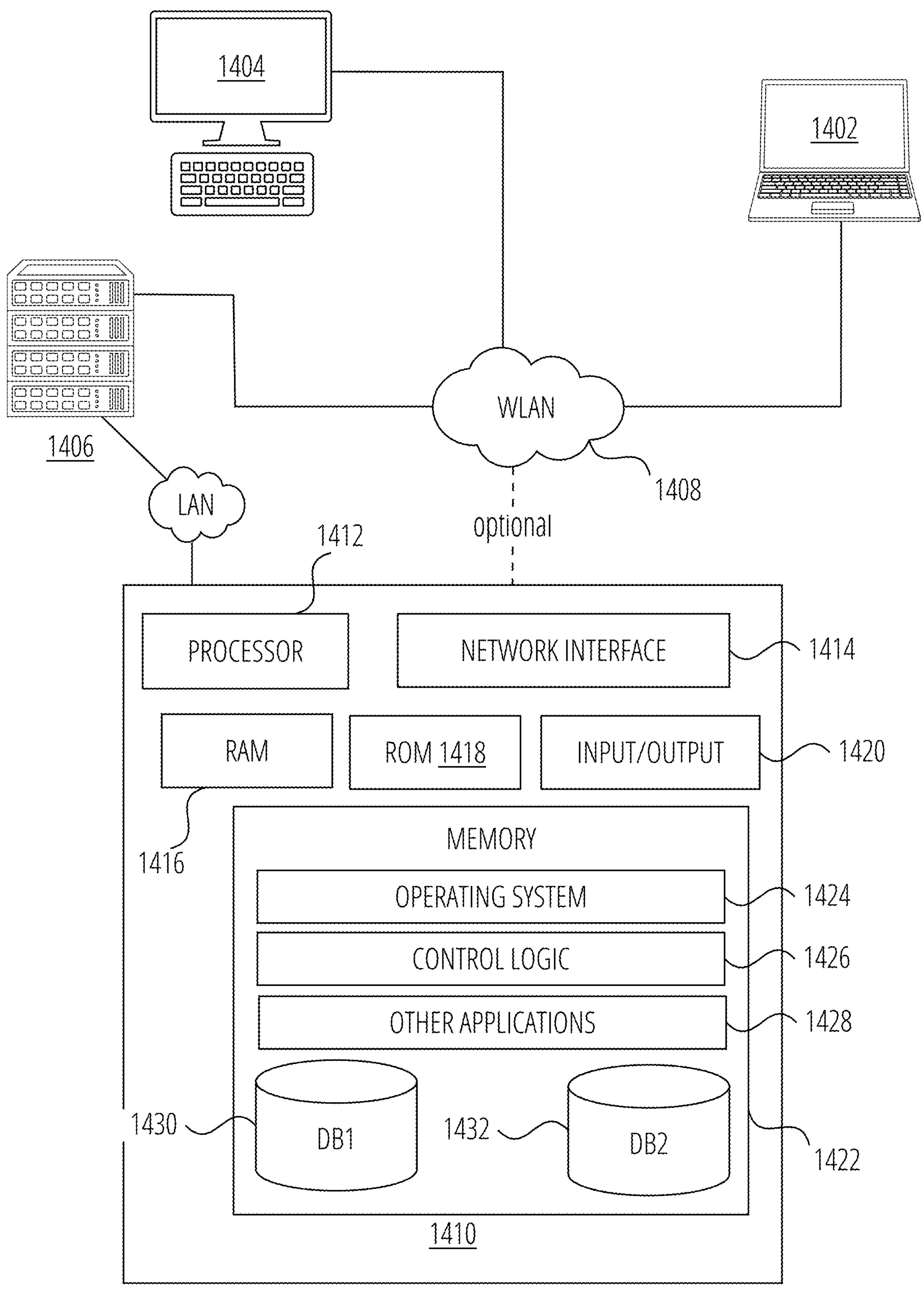
FIG. 14 depicts an illustrative computer system architecture that may be used to practice exemplary embodiments described herein.

The exemplary embodiments described herein may be performed at the client browser 224 and acquisition device 218, among other locations. An example of a device suitable for use as an acquisition device 218 and/or client browser 224, as well as various data storage devices, is depicted in FIG. 14.

FIG. 3A-FIG. 10A provide examples of graphical user interfaces suitable for use with exemplary embodiments. These interfaces generally show comparisons between one or more experimental molecule fragmentation results and a modeled or library molecule fragmentation.

The experimental results may be the result of providing a molecule (such as a DNA or RNA molecule, among other possibilities) to an MS apparatus. The output of the MS apparatus may include a mass spectrum identifying, for given detection events, the mass-to-charge ratio associated with the detection event and an intensity of the detection event. Each detection event may correspond to a particular ion that can be identified by the mass-to-charge ratio.

The modeled/library fragmentation may be generated by applying a fragmentation model that predicts how a given molecule will fragment into constituent ions. The fragmented ions of the model may be compared to the ions observed in the experimental results in order to determine whether experimental results match the modeled/library results.

Figure 3A:
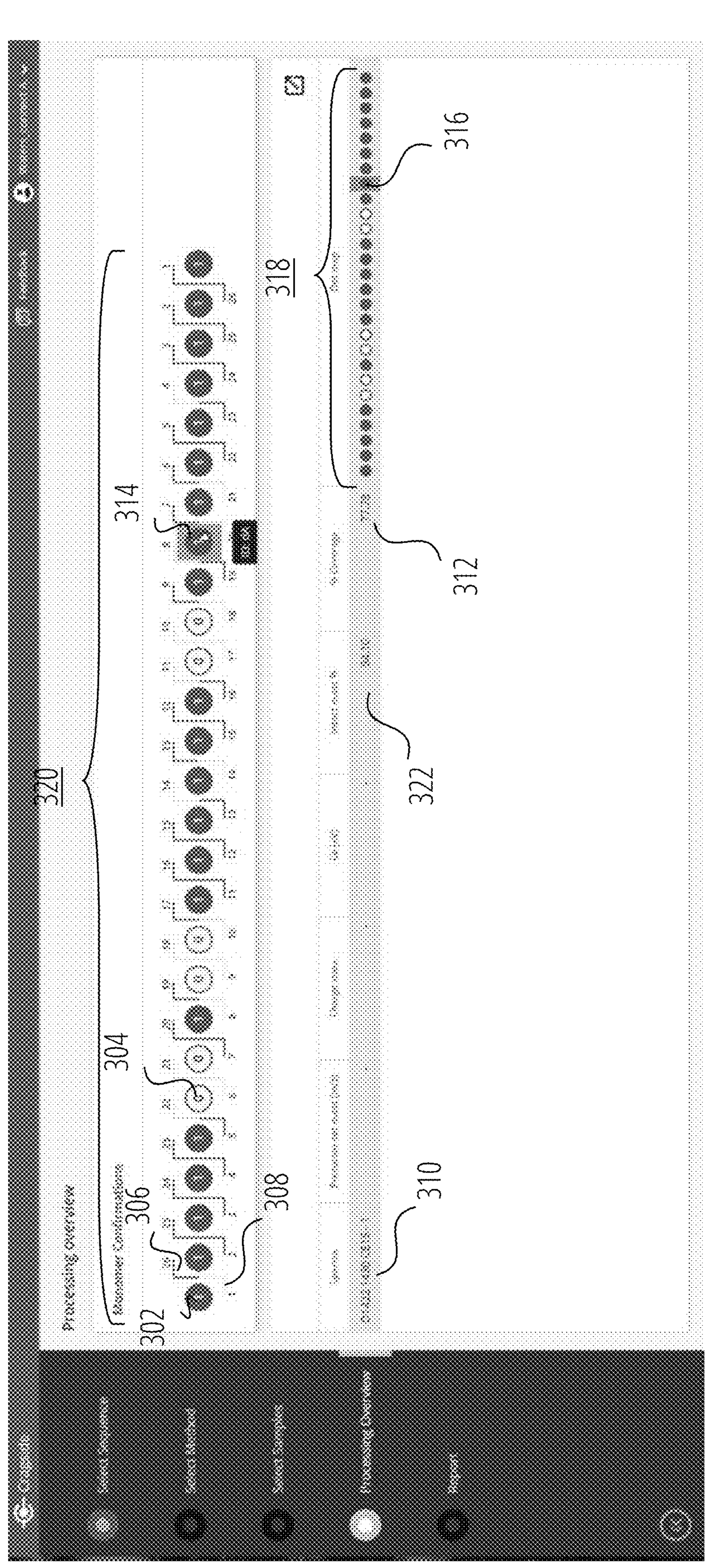
FIG. 3A depicts an exemplary user interface showing a dot map in accordance with one embodiment.

For instance, FIG. 3A shows an improved user interface for visualizing a degree of matching between a modeled fragmentation and an experimental fragmentation. The interface shows a graphical representation of modeled fragmentation 320 in the form of a dot map. The graphical representation of modeled fragmentation 320 represents the hypothetical fragmentation of a molecule into constituent ions, and may be generated through modeling and/or prior data. The modeled fragmentation may be retrieved from a preexisting library.

The graphical representation of modeled fragmentation 320 is divided into different graphical elements 302, each representing an ion resulting from the fragmentation of the molecule. As noted above, even when the modeled molecule does correspond to an experimental molecule, it is unlikely that all the hypothetical fragment ions will be observed in the experimental data. In order to allow a user to quickly judge a degree of match between the hypothetical fragmentation and the experimental fragmentation, the graphical elements 302 may be visually distinguished based on whether an ion corresponding to the hypothetical fragment ion represented by the graphical element 302 was observed in the experimental results. In this example, when a match has been detected, the corresponding graphical element 302 is filled in; when a match is not detected, the corresponding graphical element is not filled in, as is the case with negative graphical element 304. One of ordinary skill in the art will recognize that other techniques for graphically distinguishing matching vs unmatched ions may also be used.

A match may be detected when a given mass peak in the experimental data matches to a predicted mass peak within a predetermined threshold amount (e.g., within a certain window around a predicted m/z value, with an intensity above a predetermined minimum threshold). The tolerance for a match may be adjusted in a settings menu (see, e.g., FIG. 9).

The graphical representation of modeled fragmentation 320 includes forward ion indicators 306 and reverse ion indicators reverse ion indicator 308. These indicators may represent whether an ion was found in the experimental results in the forward or reverse direction (respectively) from an ion corresponding to the graphical element 302 next to the indicator. In particular, when a molecule is fragmented, it fragments at predictable locations into predictable fragment ions. Based on the predicted locations and fragment ions, it is possible to predict, on each side of the fragmentation (forward and reverse), an expected mass that should be observed for the fragment ions. When a molecule is fragmented in an experiment, the observed mass on each side of the predicted fragmentation location can be measured and compared to the predicted mass. If the two match (within a certain tolerance), the presence of the predicted ion in the forward and/or reverse direction can be confirmed; if they do not, the forward/reverse ion is not confirmed.

The interface also shows an experimental fragmentation of a molecule 310, which represents a particular experimental fragmentation carried out by an MS apparatus. Among other things, the experimental fragmentation of a molecule 310 may show a graphical representation of experimental fragmentation 318, which represents ion detections for a given experimental run (as compared to the predicted fragmentation represented by the graphical representation of modeled fragmentation 320). In this example, the graphical representation of experimental fragmentation 318 corresponds to the graphical representation of modeled fragmentation 320 because only one experimental result has been run and is therefore shown in the interface. When multiple experimental results are being compared to the modeled fragmentation, this portion of the interface would show multiple graphical representation of experimental fragmentation 318, each one showing the respective ion matches for that experimental run as compared to the modeled fragmentation (see, e.g., FIG. 5).

As part of the experimental fragmentation of a molecule 310, the interface may show a coverage percentage 312 indicating how closely the experimental fragmentation matches the modeled fragmentation. The coverage percentage 312 may be expressed in terms of a percentage, score, grade, or any other suitable means. For example, the coverage percentage 312 may be calculated by determining the percentage of the respective ion matches for an experimental run as compared to the modeled fragmentation.

The experimental fragmentation of a molecule 310 may further include an intact mass percentage 322. The intact mass percentage 322 may be generated according to an intact mass analysis that describes how closely the total molecular weight of the molecule under experimental analysis matches the theoretical molecular weight of the modeled molecule. It may be expressed in terms of a percentage, score, grade, or any other suitable means.

The interface allows a user to select a selected graphical element 314 in the graphical representation of modeled fragmentation 320 in order to highlight a corresponding graphical element 316 in the experimental results. This may allow a user to quickly determine which molecules have been matched, and to what extent, across multiple experimental runs.

Figure 3B:
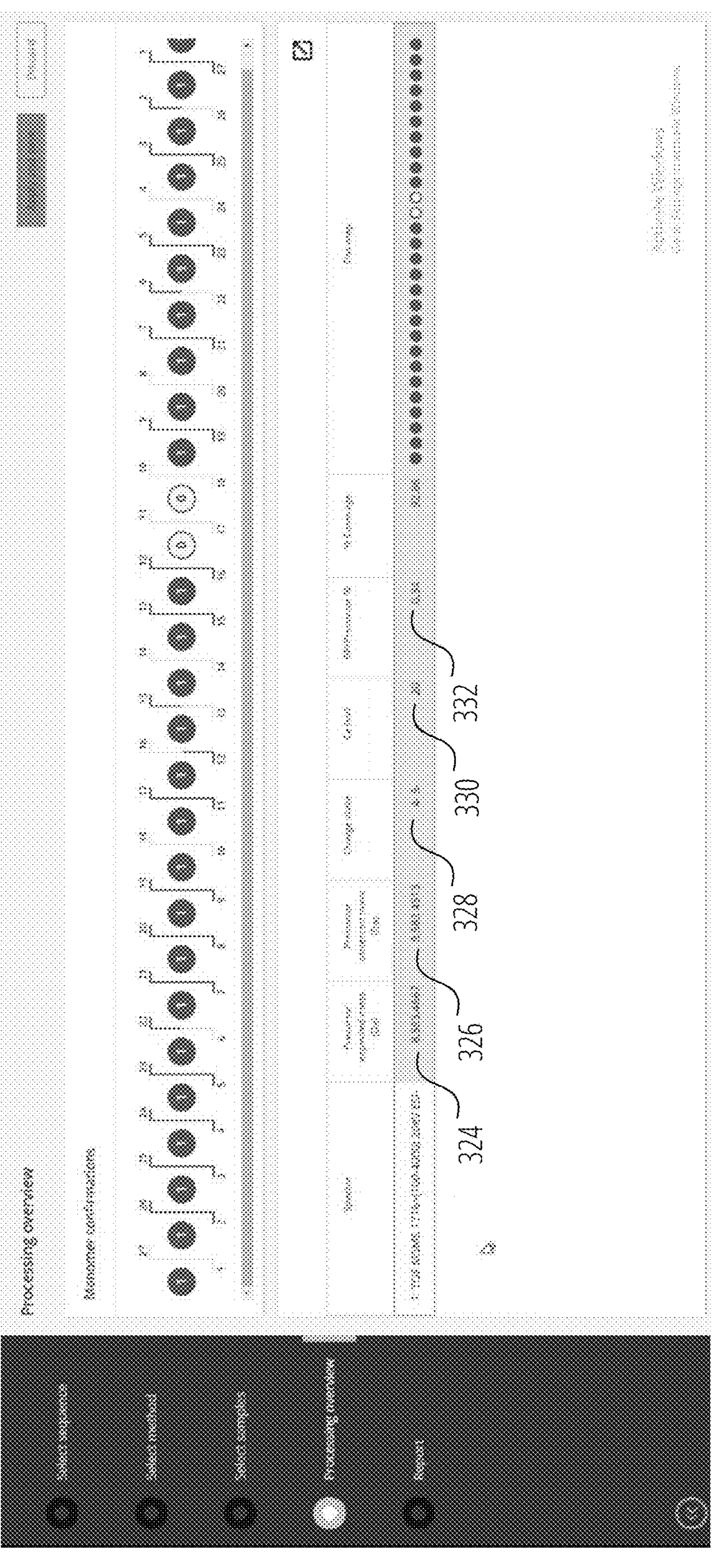
FIG. 3B depicts another version of the interface of FIG. 3A in accordance with one embodiment.

FIG. 3B depicts a version of the interface of FIG. 3A showing more information for a given experimental fragmentation of a molecule 310 (including the precursor expected mass 324, precursor observed mass 326, charge state 328, Ce value 330, and BP/Precursor percentage 332 of the molecule).

Figure 4:
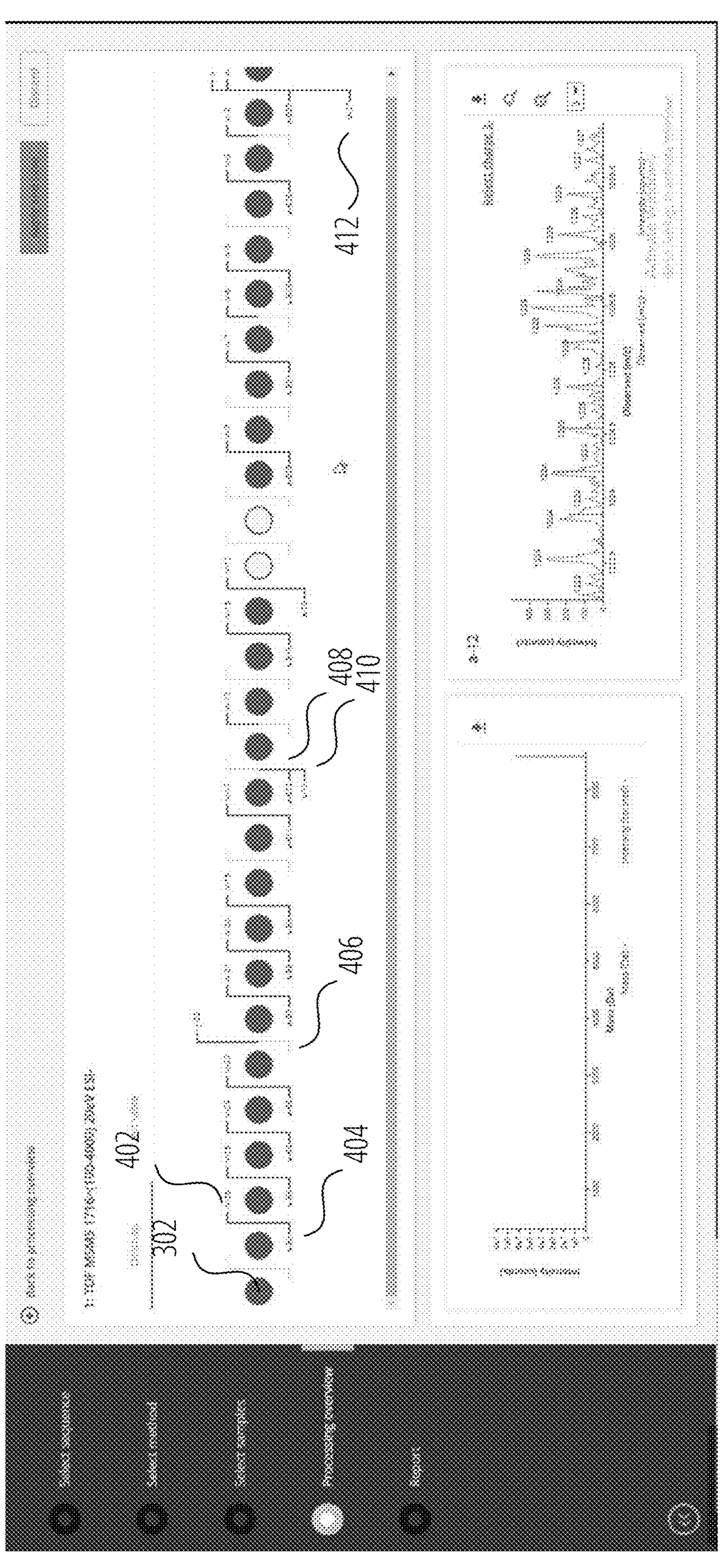
FIG. 4 depicts another interface showing an alternative representation for forward and reverse ion confirmations in accordance with one embodiment.

FIG. 4 depicts yet another interface, showing an alternative way to represent forward and reverse ion confirmations. As in the example from FIG. 3A, indicators between the graphical elements 302 are present or absent (or represented in a different color, or in some other distinguishing way) depending on whether a predicted ion was observed in the forward or reverse direction. For instance, the interface shows a forward ion confirmation 402, reverse ion confirmation 404, and reverse ion non-confirmation 406.

In this example, the ion indicators are represented as legs that extend away from the graphical element 302. The length of the leg and/or its direction may be is dependent on the ion series (e.g., a, b, c, d, a-B, w, x, y, z) that was predicted or confirmed. So, for example, a first ion series 408 (*a*-B) is presented at a first height, a second ion series 410 (*a*) is presented at a second height, and a third ion series 412 (*d*) is presented at a third height. This provides a user with an overview of the molecule; by lining up the confirmed forward/reverse ions according to height, the user can discern useful information about the molecule at a glance. Similarly, both the upward and downward directions are used for legs showing forward ion series (e.g., a, b, c, d, a-B) and reverse ion series (w, x, y, z). User-defined ions may also be added to the dot map.

Figure 5:
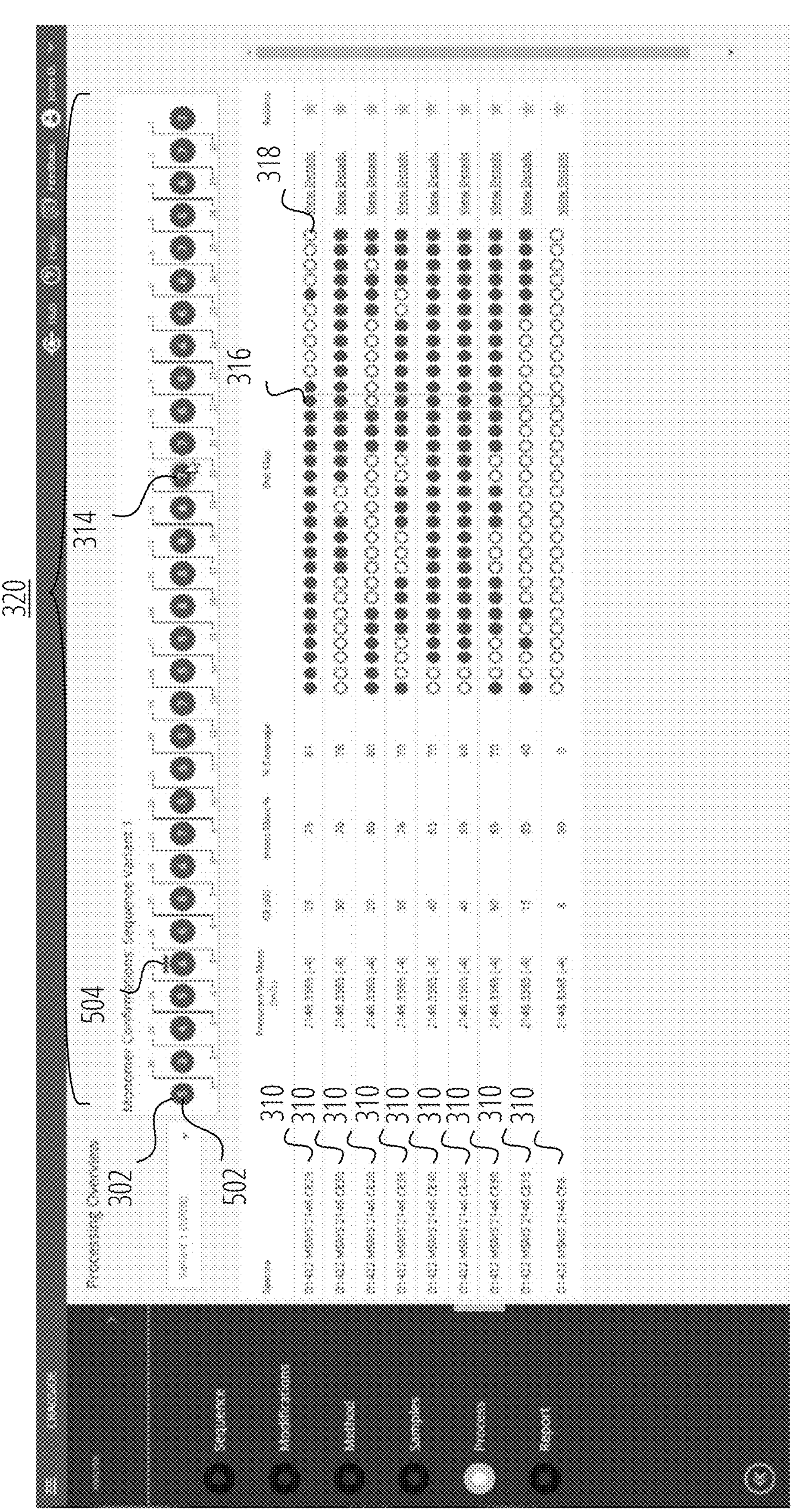
FIG. 5 depicts an exemplary user interface showing multiple accumulated experimental runs in accordance with one embodiment.

FIG. 5 depicts a version of the above-described interface showing multiple experimental runs and therefore multiple experimental fragmentations of a molecule 310. In this case, the graphical elements 302 of the graphical representation of modeled fragmentation 320 represent cumulative results from the experimental fragmentations of a molecule 310. If at least one experimental run has confirmed the presence of a given ion, the corresponding graphical element 302 in the graphical representation of modeled fragmentation 320 may be filled in (or otherwise indicated as a "hit"). The graphical element 302 may include a score 502 indicating how many times the ion corresponding to the graphical element was observed in the experimental fragmentations of a molecule 310.

The graphical representation of modeled fragmentation 320 may also include a variant indicator 504 associated with one or more of the graphical elements 302. The variant indicator 504 may indicate that an ion corresponding to the graphical element is associated with a potential modification. The modification may be, for instance, a particular molecule attached to the ion represented by the graphical element 302. Multiple different modifications may be possible for a given ion (e.g., multiple different molecules could theoretically attach to the ion). A particular combination of an ion and a specified modification may be referred to as a variant. The variant indicator 504 may indicate where variants are possible in the graphical representation of modeled fragmentation 320.

Figure 6:
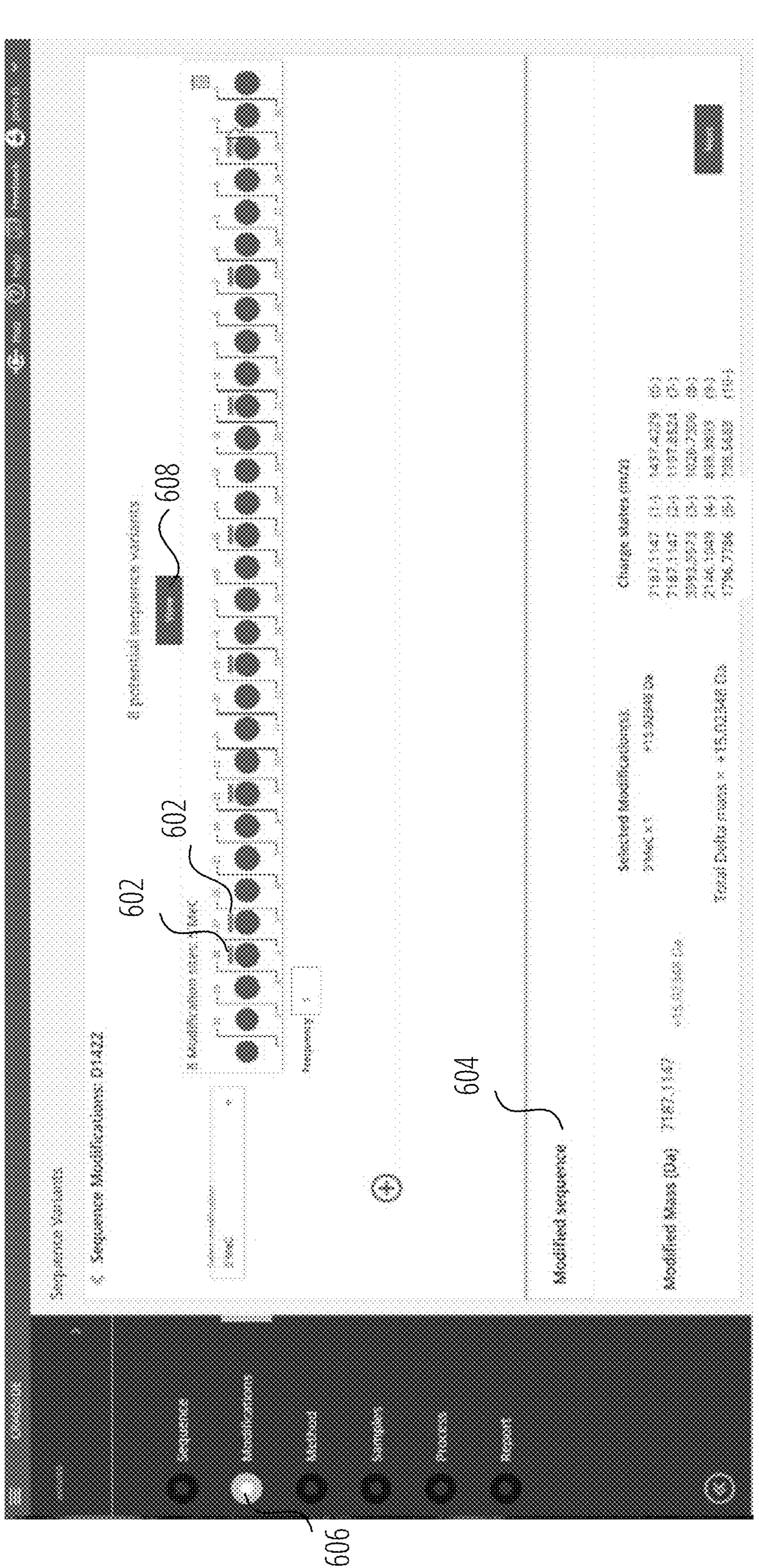
FIG. 6 depicts an exemplary user interface showing molecule modifications in accordance with one embodiment.

In some cases, it may be known that a variant may exist on a given ion, but experimental results have not yet definitively confirmed which (if any) modifications are present in the experimental sample(s). To that end, FIG. 6 shows an interface that allows a user to identify which sequence variants are present or possible. The interface of FIG. 6 may be accessed by selecting a variant page selector 606 in a menu or other interface.

The interface displays a dot map similar to the one in FIGS. 3-4. For some or all of the graphical elements, a potential variant indicator 602 may be present if a variant is possible at that location. If a particular modification has been confirmed at that location, the potential variant indicator 602 may be visually distinguished from a potential variant indicator 602 at a location where a modification is known to be possible, but the specific variant is not yet known or confirmed. For instance, a confirmed variant may be indicated by a filled-in potential variant indicator 602, or a potential variant indicator 602 in a first color, whereas an unconfirmed variant may be indicated by a hollow potential variant indicator 602 or a potential variant indicator 602 in a second color different from the first color.

A user can select one of the potential variant indicators 602, and in response variant details 604 may be shown for the selected variant. The variant details 604 may include details of the molecule as modified with any selected modifications.

In some cases, a variant may be known to exist at some combination of one or more locations. For instance, given the overall mass of the molecule, it may be known that a modification exists at at least one location. It may also be known, based on the model data, that modifications are possible at some, but potentially not all, of multiple different locations (eight, in the depicted example). The interface therefore provides a variant display element 608 that allows a user to visualize the different possible variants.

Figure 7:
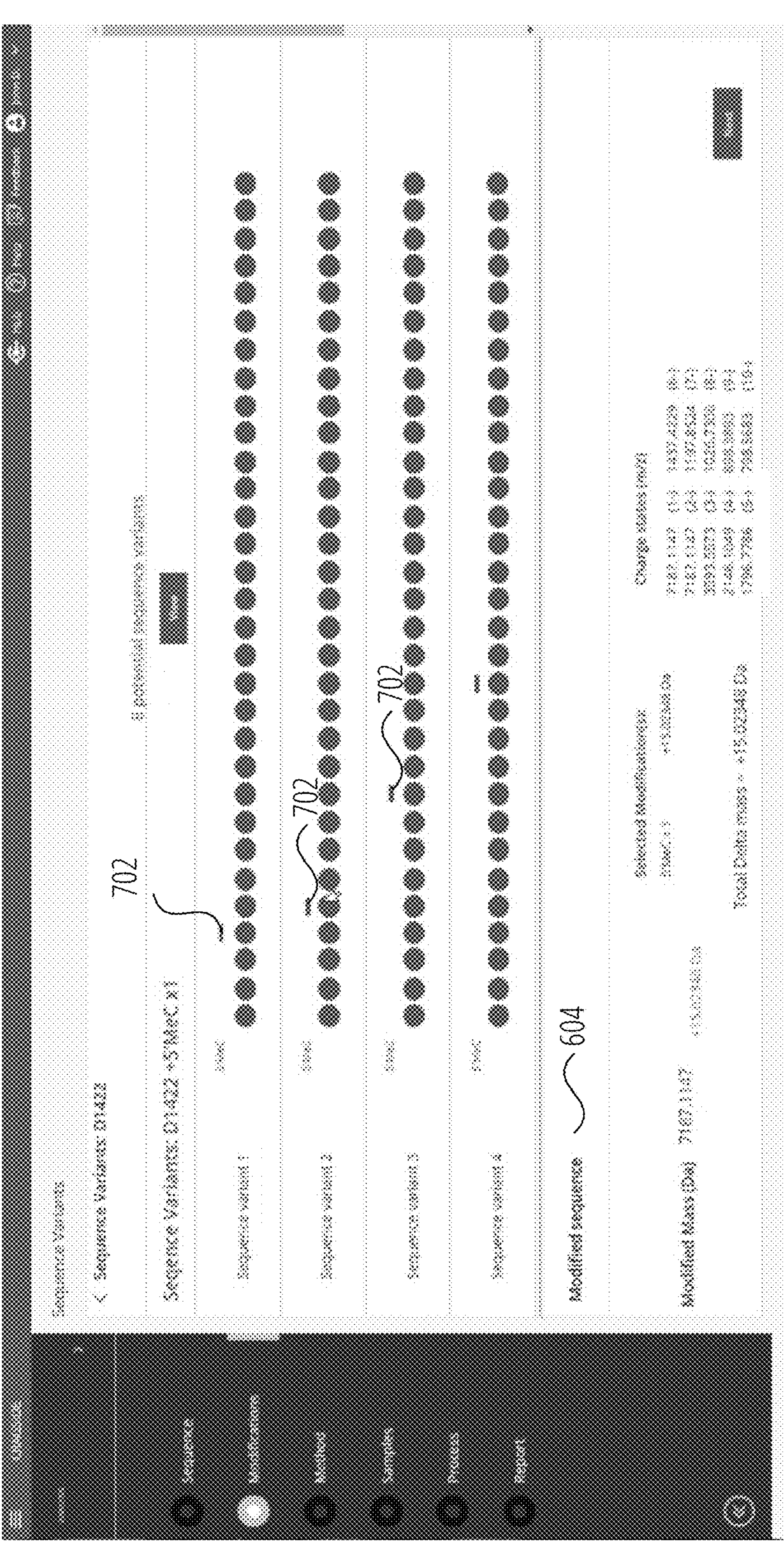
FIG. 7 depicts an exemplary user interface showing potential molecule variants in accordance with one embodiment.

Upon receiving a selection of the variant display element 608, an interface such as the one depicted in FIG. 7 may be displayed. This interface shows the different possible variants of the molecule from FIG. 6. As previously noted, that molecule was known to include a variant (based, e.g., on the mass of the molecule), but it may not be known which specific modification(s) is/are present. FIG. 7 indicates the different possible sequence variants that are possible, given what is otherwise known about the molecule. The interface includes a number of selected variant indicators 702 showing where the modification is located for the specific variant under consideration. When a user selects one of the sequence variants, the variant details 604 may be updated to show details about the variant (e.g., mass, charge states, etc.).

Figure 8:
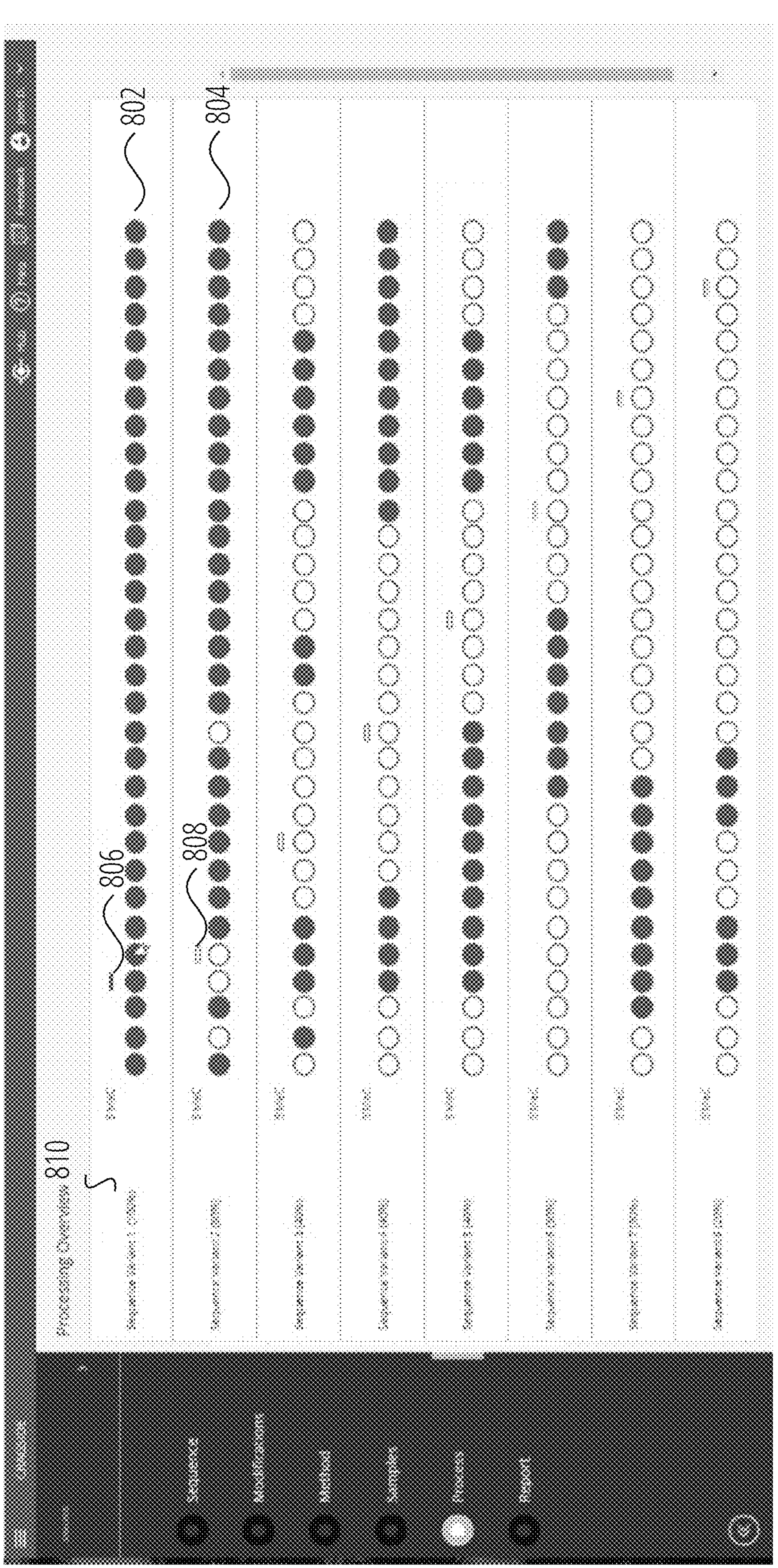
FIG. 8 depicts an exemplary user interface showing coverage for different molecule variants in accordance with one embodiment.

The system may be configured to determine, for each of the different possible variants, which one is most likely based on the observed experimental results. FIG. 8, for example, shows an interface summarizing how the possible variants from the interface of FIG. 7 match up to the experimental data.

In this case, a first potential variant 802 and a second potential variant 804 (among others) are displayed. A positive variant identification 806 on the first potential variant 802 indicates where a possible modification has been observed in the experimental data. A negative variant identification 808 on the second potential variant 804 indicates where a modification was possible, but not observed in the experimental data.

Each potential variant may be displayed with a dot map similar to the one described above. The graphical elements of the dot map may indicate where ions for each potential variant have been observed in the (cumulative) experimental data. Based on how well each of the variants matches the modeled results (which may include the observed presence of a modification and/or the presence of predicted ions), a coverage percentage 810 may be calculated. The variants may be shown in a ranked order based on the coverage percentages 810.

Figure 9:
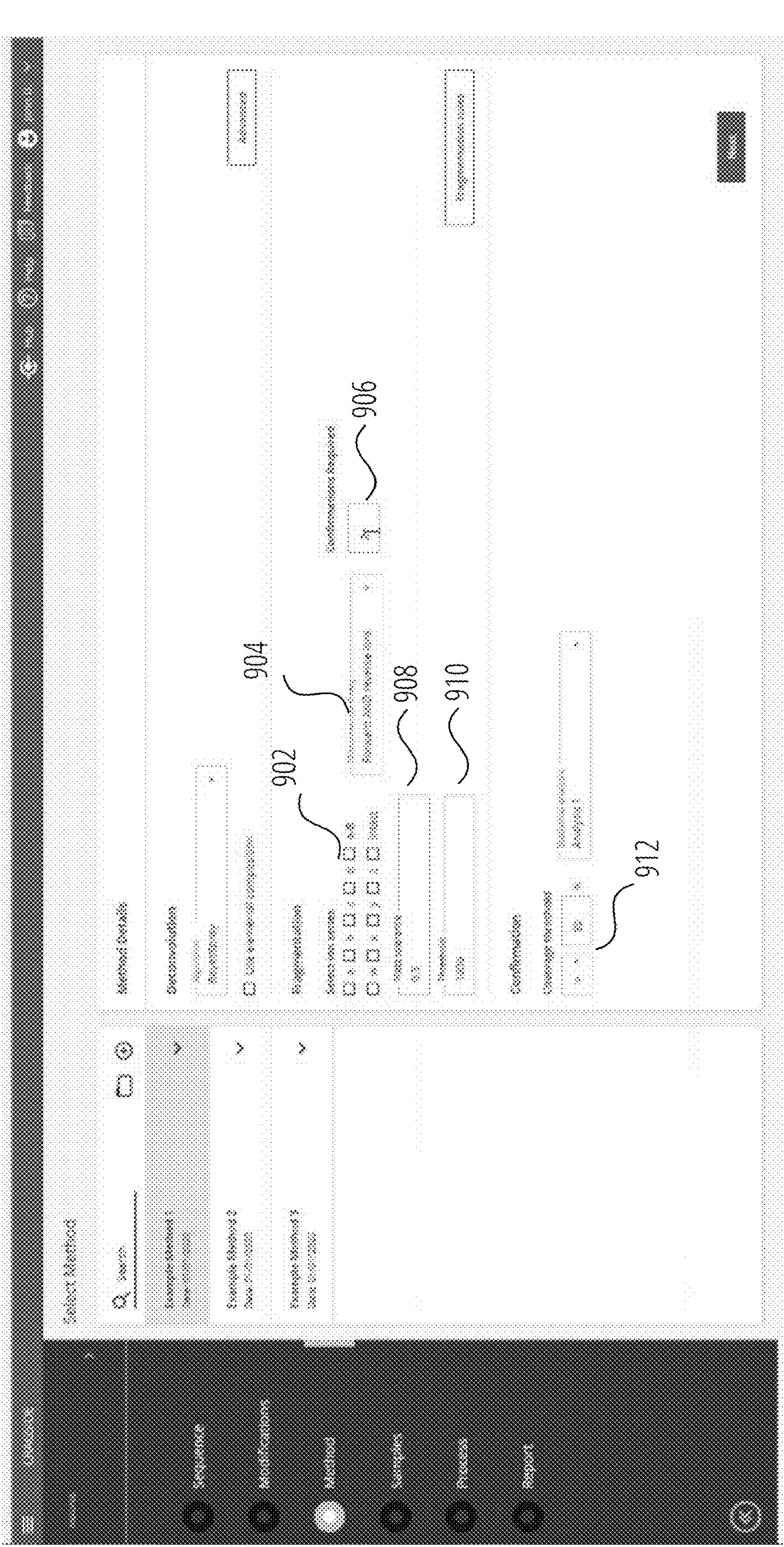
FIG. 9 depicts an exemplary configuration interface in accordance with one embodiment.

The thresholds and display options for any of the above-described interfaces may be configured in a settings interface, such as the one depicted in FIG. 9.

The interface includes an ion series selectors 902 allowing the user to select which ion series will be considered and/or displayed in the fragmentations.

A monomer confirmation requirements 904 dropdown allows a user to select when a monomer will be confirmed—e.g., when a predetermined ion/monomer is observed in the forward direction from the monomer, in the reverse direction, neither, or both. This allows matches to be identified based on the overall structure of the molecule(s), rather than simply the presence of certain ions. Thus, if certain fragments are seen, it may be necessary to see those fragments in a particular order to be able to confirm the presence of a certain monomer.

A confirmation amount required 906 may describe a number of monomer confirmations (as defined by the monomer confirmation requirements 904) that may be required in order to confirm that a modeled fragmentation matches an experimental fragmentation.

A mass tolerance 908 may define the window around the mass-to-charge ratios for a given ion to be confirmed as being present, while a threshold value 910 may define the minimum intensity required to confirm the ion.

A coverage threshold 912 defines how closely the fragmentation must match the experimental results (which may be accumulated experimental results) before a match is indicated.

Figure 10A:
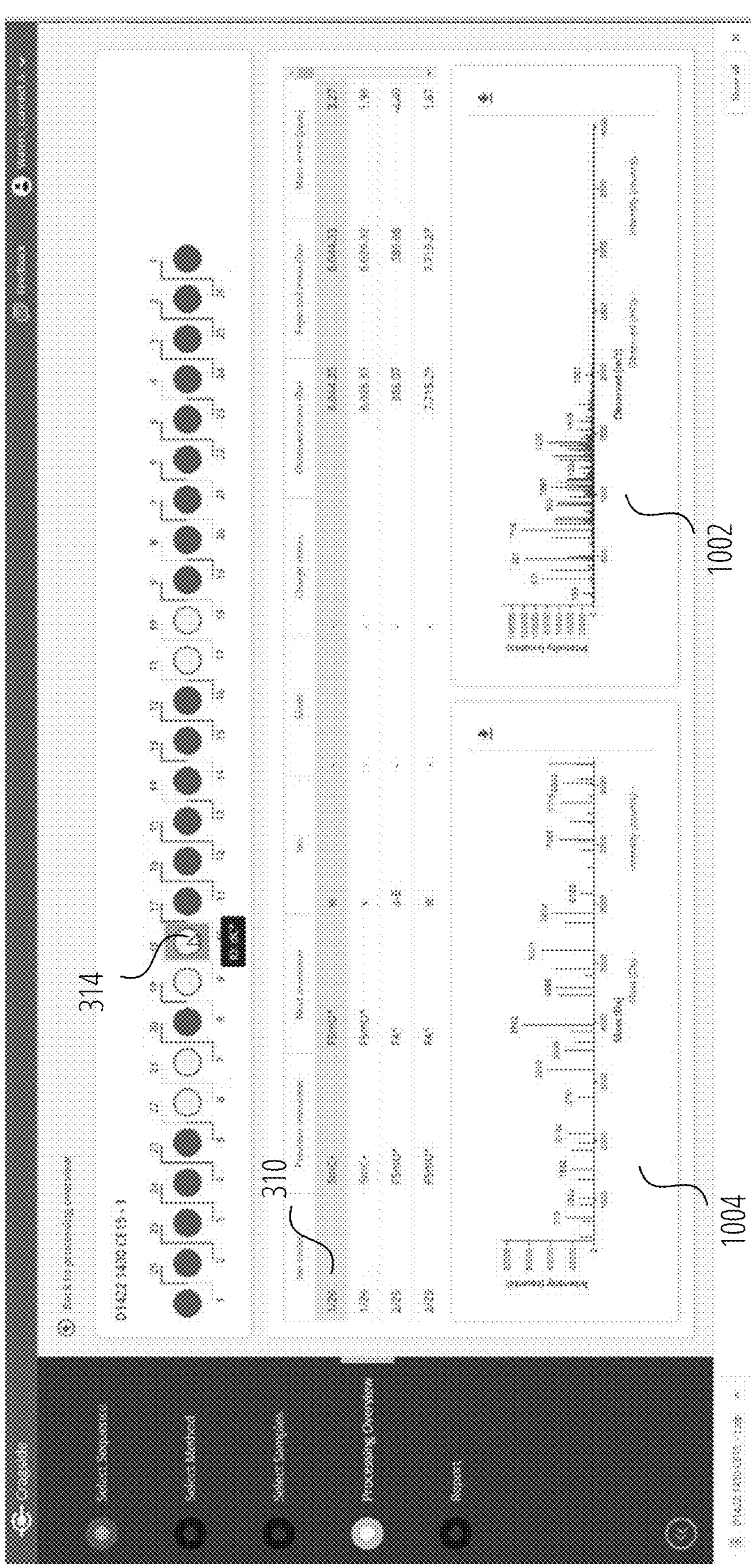
FIG. 10A depicts an exemplary interface showing experimental mass spectrum data in accordance with one embodiment.

The interfaces described above also allow a user to drill down into the experimental data that supports whether a given ion represents a hit or a miss. For instance, FIG. 10A shows an example of an interface where a user has selected a selected graphical element 314. In this case, the graphical element is not filled in, indicating a "miss" (i.e., the data does not support a finding that the ion was observed in the experimental data, based on the settings defined in the interface of FIG. 9).

In response to receiving a selection of the graphical element, the interface may display a corresponding predicted mass spectrum 1004, which indicates the mass spectrum that was predicted to be observed based on the model. For comparison, the observed mass spectrum 1002 from the experimental data may be displayed next to the predicted mass spectrum 1004.

Figure 10B:
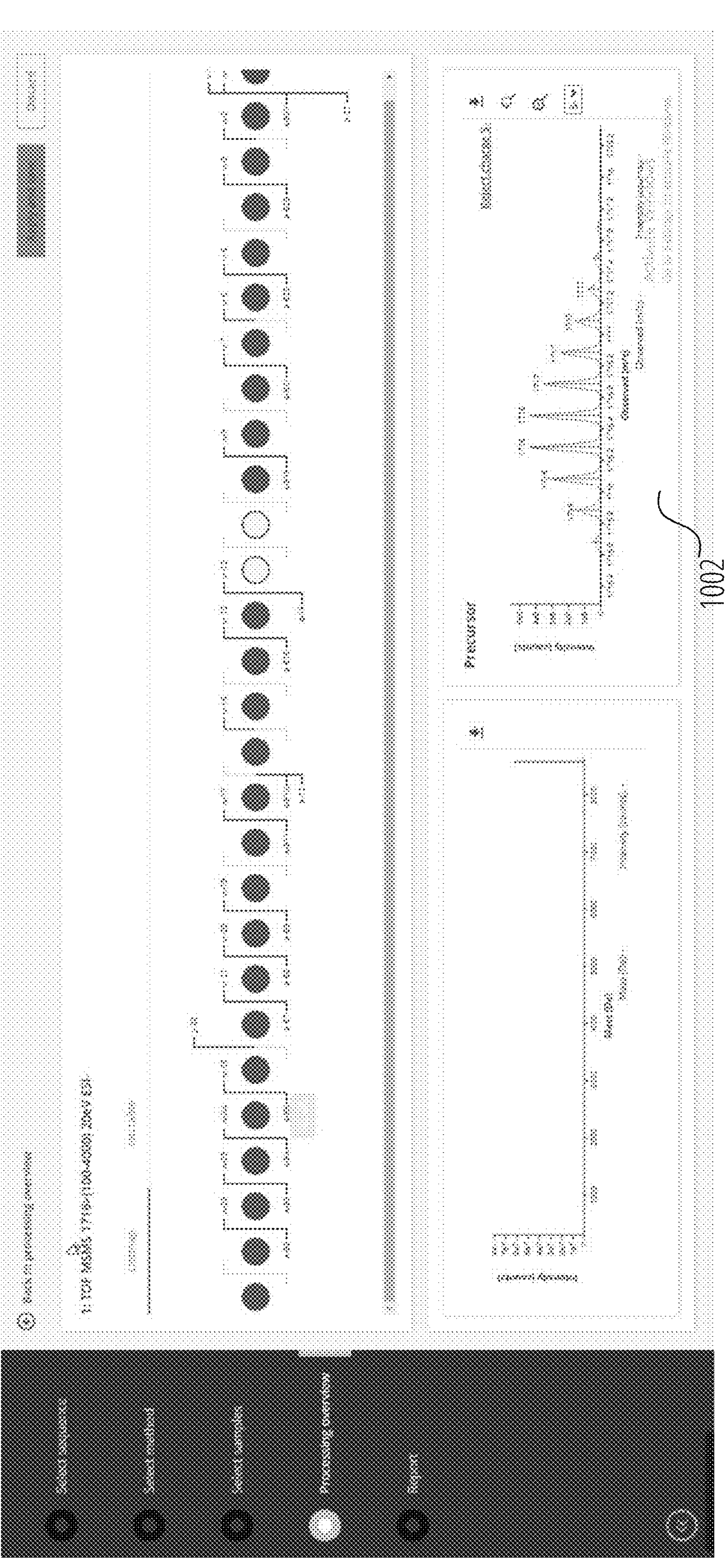
FIG. 10B illustrates another interface showing experimental mass spectrum data in accordance with one embodiment.

FIG. 10B depicts another example of an interface showing the observed mass spectrum 1002. In this case, no particular graphical element 302 is selected, and so the observed mass spectrum 1002 is the mass spectrum for the entire precursor ion. By selecting a portion of the graph in the observed mass spectrum 1002, a user can zoom in on that portion, where the observed mass spectrum 1002 is updated to show a smaller range of masses in more detail.

Figure 11A:
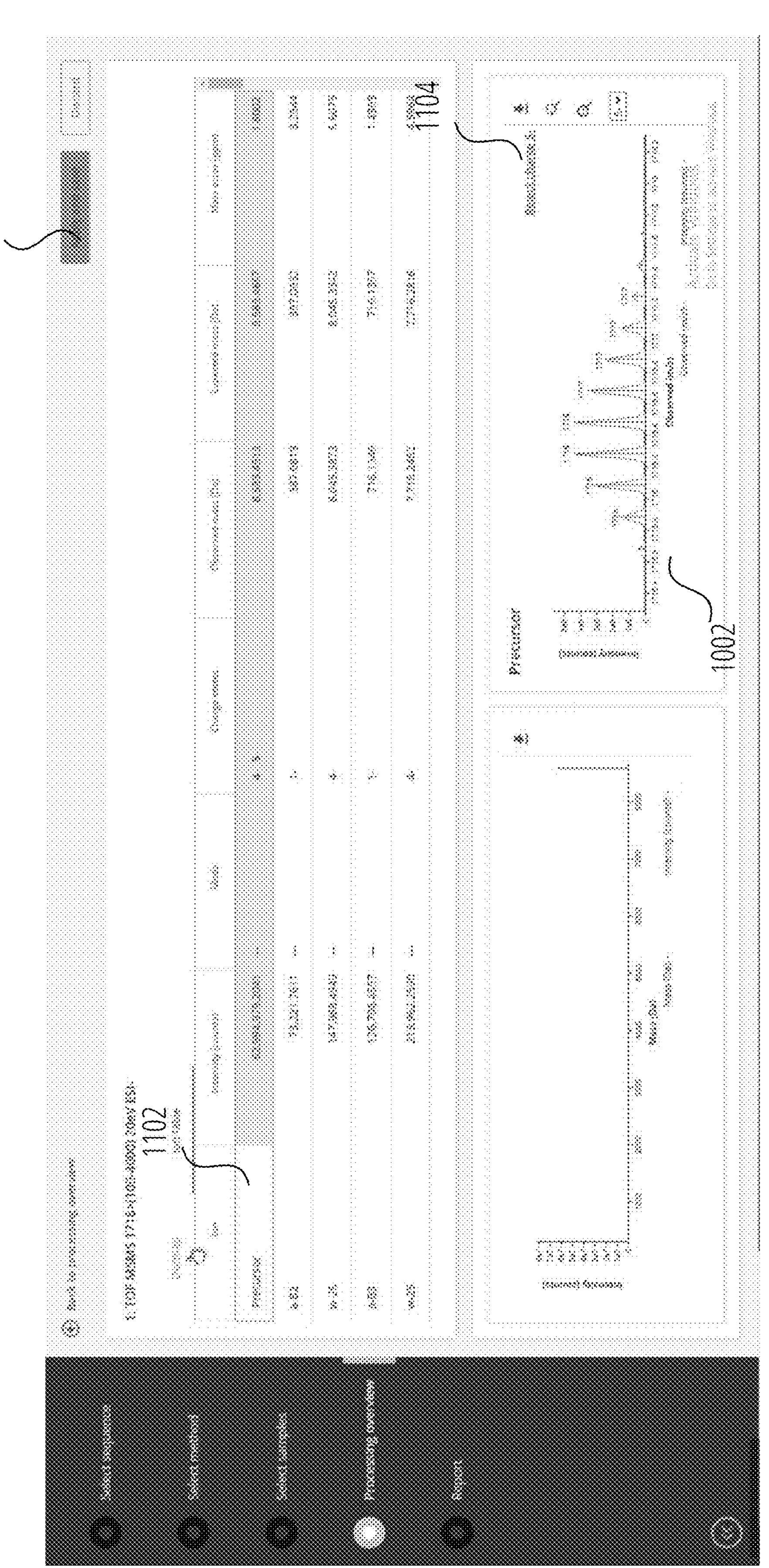
FIG. 11A is another interface for viewing experimental mass spectrum data in accordance with one embodiment.

FIG. 11A shows another way to view an observed mass spectrum 1002. In this case, an ion table is shown in the upper portion of the interface instead of the dot map (this interface can be displayed in response to receiving a selection of the "Ion Table" tab). The ion table includes each of the ions in the modeled fragmentation, including the precursor ion. A user can select a selected ion 1102 in the table in order to cause the corresponding observed mass spectrum 1002 to be displayed.

Figure 11B:
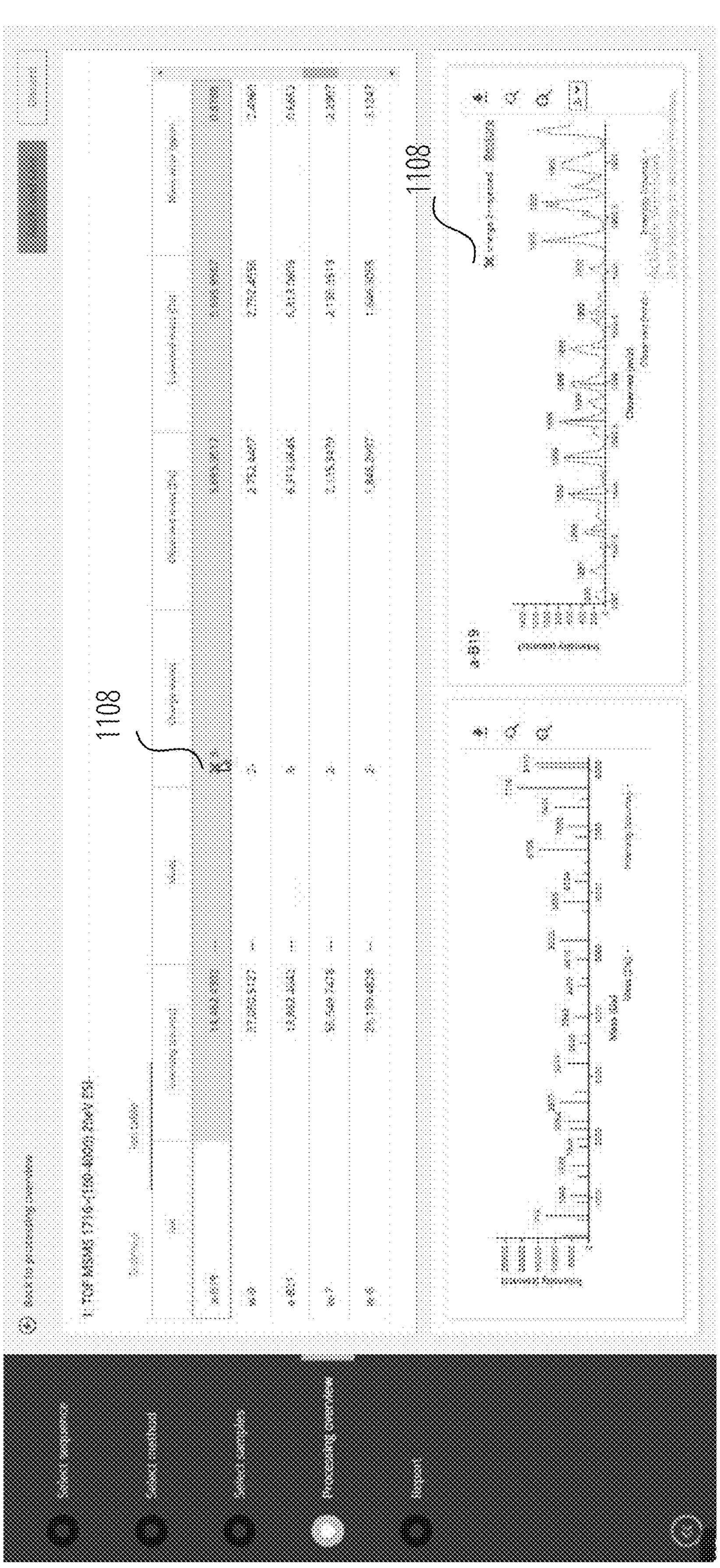
FIG. 11B is another interface for viewing experimental mass spectrum data in accordance with one embodiment.

When a modeled ion is confirmed by the experimental data, the interface may also includes a charge rejection element 1104 that allows a user to reject the confirmation. By selecting the charge rejection element 1104, the user can queue one or more rejections, which can then be confirmed one-at-a-time or in bulk by selecting a confirmation element 1106. Selecting the confirmation element 1106 may cause the system to set the ions as being unconfirmed in the experimental data, and may cause any respective interfaces to be updated. For example, the dot map may be updated so that a graphical element 302 changes from a confirmed graphical element 302 to a negative graphical element 304 (see, e.g., FIG. 3A). In the ion table, a user-selected disconfirmation may be indicated by a charge rejection indicator 1108, as shown in FIG. 11B.

Figure 12:
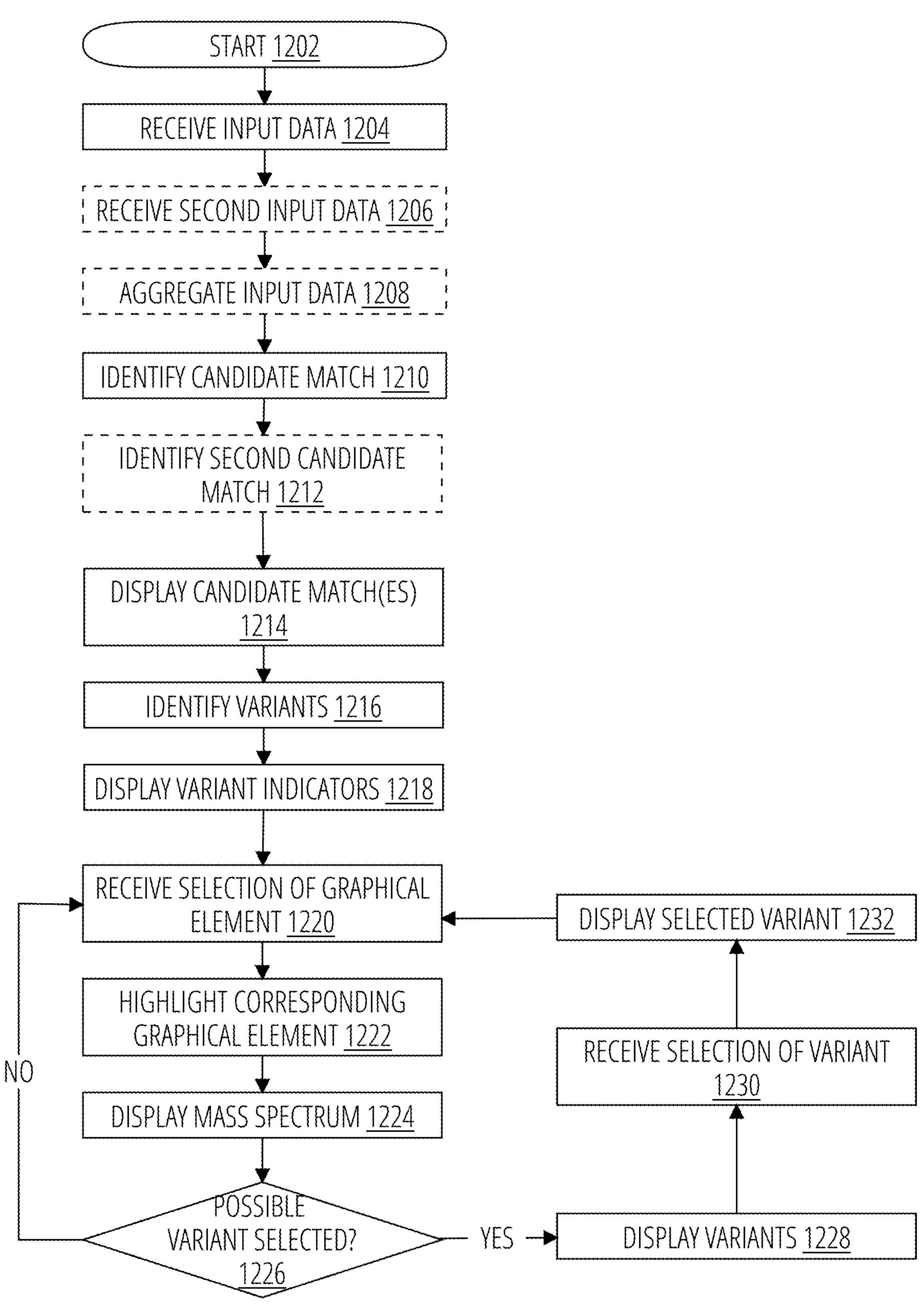
FIG. 12 is a flowchart depicting exemplary logic for displaying and updating an interface in accordance with one embodiment.

The above-described interfaces may be displayed as part of a computer-implemented method. FIG. 12 is a flowchart depicting exemplary logic for implementing such a method.

The logic may be embodied as instructions stored on a computer-readable medium configured to be executed by a processor. The logic may be implemented by a suitable computing system configured to perform the actions described below.

Processing may begin at block 1202. In block 1204, the system may receive input data. The input data may include MS experimental data representing a fragmentation of an experimental sample. The input data may correspond to a fragmentation of a target molecule, where the input data is being compared against a modeled or stored fragmentation pattern of a molecule to determine if the experimental data matches the modeled/library pattern.

Optionally, in block 1206, second (or more) input data may be received. The second input data may correspond to additional experimental runs testing the target molecule (e.g., additional samples of the same target molecule). In block 1208, the input data may be rolled up or aggregated. The mass peaks in the spectra from each experimental run may be represented together in a common structure so that, if a mass peak is present in any one of the experimental runs, it will be represented in the common structure.

In block 1210, the system may identify a candidate match from a library of model fragmentation patterns. This may involve receiving a selection (e.g., a user selection) of a model fragmentation pattern that the input data is to be compared to, or automatically comparing the fragmentation pattern of the input data to the fragmentation patterns of the library. A coverage score may be calculated for each fragmentation pattern, and the fragmentation pattern from the library with the highest degree of coverage may be selected for comparison.

In some embodiments, a coverage score may be calculated for each fragmentation pattern, and the fragmentation pattern from the library with the highest degree of coverage may be selected for comparison. The system may require that certain ions be observed in a particular order in order to make a match more likely.

The coverage score may be calculated based on a statistical analysis that attempts to match each fragment individually (e.g., looking for the best possible coverage) and/or combinations of fragments in a specified order. The statistical analysis may generate a confidence score indicating how likely the system considers the modeled data to be a match for the experimental data. The system may select, as the model fragmentation for comparison to the experimental data, the model having the highest likelihood. In some embodiments, the likelihood may need to exceed a predetermined threshold value in order to be considered a match. The system may account for possible variants when identifying which candidate match best fits the observed data.

The statistical analysis may further consider, for a given model candidate, a likelihood that the experimental data would match a different model candidate. If this likelihood exceeds a predetermined threshold, the system may attempt to match the experimental data to a different model candidate.

In block 1212, the system may optionally identify a second candidate match from the library of model fragmentation patterns. The second candidate match may be a variant of the first candidate match.

In block 1214, the system may display the candidate match(es) on an interface such as the one shown in FIG. 3A et seq. The interface may show a dot map such as the graphical representation of modeled fragmentation 320, with graphical elements visually distinguished based on whether ions corresponding to the visual elements were observed in the experimental data. Whether an ion is flagged as a hit or a miss may be configured based on the settings as described above (particularly with reference to FIG. 9). In some embodiments, a confirmation may be based on data about an individual ion; in others, confirmation may require that ions be observed in a particular pattern (in the forward and/or reverse direction).

In block 1216, the system may identify variants of the candidate match. The variants may be identified and flagged in the library in which the candidate matches are stored. In block 1218, the system may display variants, such as by adding a variant indicator to the graphical elements in the graphical representation of modeled fragmentation 320. In some embodiments, the variants may be displayed in a variant interface such as the ones depicted in FIG. 6-FIG. 8. The variants may be displayed in response to a user selecting a variant page selector 606.

In block 1220, the system may receive a selection of one of the graphical elements from the graphical representation of modeled fragmentation 320. In block 1222, the system may highlight corresponding graphical elements in the experimental data. The system may correlate the predicted ion from the model data to an observed ion in the experimental data (e.g., based on mass or mass-to-charge ratio).

In block 1224, the system may display a mass spectrum associated with the model and/or the experimental results. The mass spectrum of the model may be generated by mapping the ions in the modeled fragmentation to a corresponding known mass or mass-to-charge ratio. The system may generate a peak list that accounts for the abundance of various isotopes for the different chemical elements making up the ions. The system may perform isotope modeling in order to account for the presence of the different isotopes in different molecules of the same chemical.

In decision block 1226, the system may determine whether the selection made at block 1220 was a selection of a graphical element corresponding to a possible variant. If not, processing may revert to block 1220 and may await a further selection. If so, processing may proceed to block 1228, where the possible variants identified in block 1216 may be displayed in an interface similar to the ones shown above in FIG. 6-FIG. 8.

In block 1230, the system may receive a selection of one of the variants, and in block 1232 may display details of the selected variant. Processing may then revert to block 1220 to await a further selection.

Figure 13:
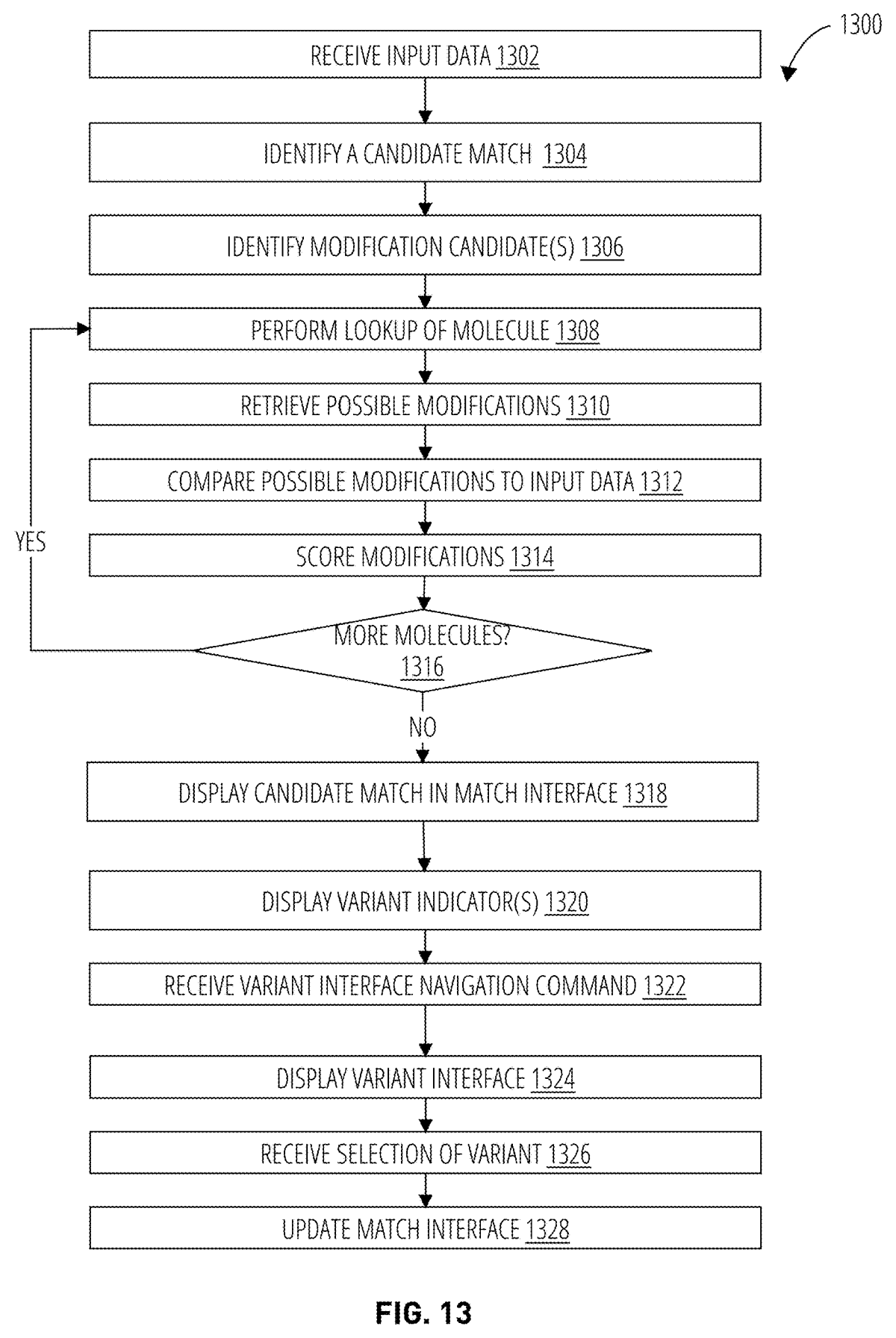

FIG. 13 is a flowchart depicting exemplary variant display logic 1300 for identifying and displaying model variants. The logic may be embodied as instructions stored on a computer-readable medium configured to be executed by a processor. The logic may be implemented by a suitable computing system configured to perform the actions described below.

In block 1302, variant display logic 1300 receives input data representing a fragmentation of a molecule into a plurality of experimental fragments. The input data may include MS experimental data representing a fragmentation of an experimental sample. The input data may correspond to a fragmentation of a target molecule, where the input data is being compared against a modeled or stored fragmentation pattern of a molecule to determine if the experimental data matches the modeled/library pattern.

Optionally, second (or more) input data may be received. The second input data may correspond to additional experimental runs testing the target molecule (e.g., additional samples of the same target molecule). In block 1208, the input data may be rolled up or aggregated. The mass peaks in the spectra from each experimental run may be represented together in a common structure so that, if a mass peak is present in any one of the experimental runs, it will be represented in the common structure.

In block 1304, variant display logic 1300 compares the fragmentation to a library of modeled fragmentations to identify a candidate match comprising a plurality of modeled fragments. This may involve receiving a selection (e.g., a user selection) of a model fragmentation pattern that the input data is to be compared to, or automatically comparing the fragmentation pattern of the input data to the fragmentation patterns of the library. A coverage score may be calculated for each fragmentation pattern, and the fragmentation pattern from the library with the highest degree of coverage may be selected for comparison.

In some embodiments, a coverage score may be calculated for each fragmentation pattern, and the fragmentation pattern from the library with the highest degree of coverage may be selected for comparison. The system may require that certain ions be observed in a particular order in order to make a match more likely.

The coverage score may be calculated based on a statistical analysis that attempts to match each fragment individually (e.g., looking for the best possible coverage) and/or combinations of fragments in a specified order. The statistical analysis may generate a confidence score indicating how likely the system considers the modeled data to be a match for the experimental data. The system may select, as the model fragmentation for comparison to the experimental data, the model having the highest likelihood. In some embodiments, the likelihood may need to exceed a predetermined threshold value in order to be considered a match. The system may account for possible variants when identifying which candidate match best fits the observed data.

The statistical analysis may further consider, for a given model candidate, a likelihood that the experimental data would match a different model candidate. If this likelihood exceeds a predetermined threshold, the system may attempt to match the experimental data to a different model candidate.

In block 1306, variant display logic 1300 identifies that a selected one of the modeled fragments is capable of supporting a modification. One exemplary technique for identifying modification candidates is described in connection with block 1308—decision block 1316.

In block 1308, the variant display logic 1300 may consider a first or next fragment in the model. The fragment may be a molecule, and the variant display logic 1300 may look up the fragment in a database or library. The database or library may include a list of molecules and may identify, for each molecule, the modifications that can be supported by the molecule. For instance, the database or library may identify that the molecule can serve as a base or attachment point to which other molecules may attach. The library or database may indicate which attaching molecules are capable of attaching to the fragment, as well as other information about the attaching molecules (e.g., configuration, orientation, mass, charge, etc.).

Each fragment may be associated with zero or more possible modifications stored in the library or database. In block 1310, the variant display logic 1300 may retrieve the list of possible modifications that could be applied to the fragment under consideration.

Although many different variants (a fragment molecule that has been modified by a modification) may be possible for any given fragment, only some of them may match the experimental data retrieved in block 1302. Therefore, in block 1312, the variant display logic 1300 may compare the variants to the input experimental data to determine how well a possible modification matches the data that was observed experimentally. The variant display logic 1300 may compare, for instance the mass of the fragment (as modified by the modification) to the observed mass of the corresponding fragment in the experimental data, the charge of the modified fragment to the observed charge, the mass-to-charge ratios of the model and experimental fragments, the total masses of the modeled molecule (including all fragments) and the experimental molecule, the total charges of the molecules, or the total mass-to-charge ratios, as well as other types of information (including structural data, such as collision cross section data). The variant display logic 1300 may also consider the unmodified fragment, to determine if it is a better match for the data than any variant.

In block 1314, the variant display logic 1300 may assign a value, such as a percentage or score, to each of the possible modifications (as well as the base, unmodified version). If the value is below a predetermined minimum threshold value, the corresponding modification may be considered sufficiently unlikely and may be excluded from further analysis or display. The remaining possible modifications may be ranked based on the values in order to identify which modifications best fit the observed experimental data. If the score for one of the modifications exceeds a predetermined threshold confirmation value (indicating that the modification is highly likely to be present), then the modification may be identified as confirmed and may be displayed accordingly in the interface (e.g., with a solid bar indicating a confirmed variant instead of a hollow bar indicating a possible variant).

In decision block 1316, the variant display logic 1300 determines if there are more fragment molecules in the modeled fragmentation to be considered. If so, processing may return to block 1308 and the next molecule may be selected for consideration. If not, processing may proceed to block 1318.

In block 1318, variant display logic 1300 displays a graphical representation of the candidate match. The variant display logic 1300 may display the candidate match(es) on an interface such as the one shown in FIG. 3A et seq. The interface may show a dot map such as the graphical representation of modeled fragmentation 320, with graphical elements visually distinguished based on whether ions corresponding to the visual elements were observed in the experimental data. Whether an ion is flagged as a hit or a miss may be configured based on the settings as described above (particularly with reference to FIG. 9). In some embodiments, a confirmation may be based on data about an individual ion; in others, confirmation may require that ions be observed in a particular pattern (in the forward and/or reverse direction).

In block 1320, the variant display logic 1300 may, for any viable modifications identified in block 1314, update a graphical element corresponding to the modification to include a variant indicator. The variant indicator may visually distinguish the selected one of the modeled fragments from a modeled fragment not capable of supporting the modification. For example, the variant display logic 1300 may display an interface such as the one depicted in FIG. 5.

The variants for different fragments may be considered in combination with each other. For example, it may be known (based on the masses included in the input data) that at least one variant is present, but multiple different combinations of variants might fit the observed data. In this case, the different combinations may be flagged as possible variants. For instance, the variant display logic 1300 may display a possible or unconfirmed variant indicator on multiple fragments. If one of the variants is confirmed (e.g., through further data or user selection), then the interface may update to show the confirmed variant and to remove any variants which no longer fit the observed data.

In block 1322, the variant display logic 1300 may receive a variant interface navigation command requesting to navigate to a dedicated variant interface such as the one shown in FIG. 6-FIG. 7. For example, the variant display logic 1300 may receive a selection of the variant page selector 606, causing the interface to be updated (at block 1324) to show an overview of possible variants (as depicted in FIG. 6). Upon receiving a further selection of the variant display element 608, the interface might further be updated to show a list of the possible variants (see, e.g., FIG. 7) in a ranked order as determined by the score computed in block 1314.

In block 1326, the variant display logic 1300 may receive a selection of a variant from among the possible variants to be further analyzed. In response, at block 1328 the variant display logic 1300 may update the display of the candidate match from block 1318 to incorporate the selected variant. For example, the graphical element 302 corresponding to the variant may be updated to show whether the variant has been confirmed in the experimental data, and the score 502 may be updated to show how many of the experimental runs included a confirmation of the variant.

FIG. 14 illustrates one example of a system architecture and data processing device that may be used to implement one or more illustrative aspects described herein in a standalone and/or networked environment. Various network nodes, such as the data server 1410, web server 1406, computer 1404, and laptop 1402 may be interconnected via a wide area network 1408 (WAN), such as the internet. Other networks may also or alternatively be used, including private intranets, corporate networks, LANs, metropolitan area networks (MANs) wireless networks, personal networks (PANs), and the like. Network 1408 is for illustration purposes and may be replaced with fewer or additional computer networks. A local area network (LAN) may have one or more of any known LAN topology and may use one or more of a variety of different protocols, such as ethernet. Devices data server 1410, web server 1406, computer 1404, laptop 1402 and other devices (not shown) may be connected to one or more of the networks via twisted pair wires, coaxial cable, fiber optics, radio waves or other communication media.

Computer software, hardware, and networks may be utilized in a variety of different system environments, including standalone, networked, remote-access (aka, remote desktop), virtualized, and/or cloud-based environments, among others.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 1410, web server 1406, and client computer 1404, laptop 1402. Data server 1410 provides overall access, control and administration of databases and control software for performing one or more illustrative aspects described herein. Data server data server 1410 may be connected to web server 1406 through which users interact with and obtain data as requested. Alternatively, data server 1410 may act as a web server itself and be directly connected to the internet. Data server 1410 may be connected to web server 1406 through the network 1408 (e.g., the internet), via direct or indirect connection, or via some other network. Users may interact with the data server 1410 using remote computer 1404, laptop 1402, e.g., using a web browser to connect to the data server 1410 via one or more externally exposed web sites hosted by web server 1406. Client computer 1404, laptop 1402 may be used in concert with data server 1410 to access data stored therein, or may be used for other purposes. For example, from client computer 1404, a user may access web server 1406 using an internet browser, as is known in the art, or by executing a software application that communicates with web server 1406 and/or data server 1410 over a computer network (such as the internet).

Servers and applications may be combined on the same physical machines, and retain separate virtual or logical addresses, or may reside on separate physical machines. FIG. 14 illustrates just one example of a network architecture that may be used, and those of skill in the art will appreciate that the specific network architecture and data processing devices used may vary, and are secondary to the functionality that they provide, as further described herein. For example, services provided by web server 1406 and data server 1410 may be combined on a single server.

Each component data server 1410, web server 1406, computer 1404, laptop 1402 may be any type of known computer, server, or data processing device. Data server 1410, e.g., may include a processor 1412 controlling overall operation of the data server 1410. Data server 1410 may further include RAM 1416, ROM 1418, network interface 1414, input/output interfaces 1420 (e.g., keyboard, mouse, display, printer, etc.), and memory 1422. Input/output interfaces 1420 may include a variety of interface units and drives for reading, writing, displaying, and/or printing data or files. Memory 1422 may further store operating system software 1424 for controlling overall operation of the data server 1410, control logic 1426 for instructing data server 1410 to perform aspects described herein, and other application software 1428 providing secondary, support, and/or other functionality which may or may not be used in conjunction with aspects described herein. The control logic may also be referred to herein as the data server software control logic 1426. Functionality of the data server software may refer to operations or decisions made automatically based on rules coded into the control logic, made manually by a user providing input into the system, and/or a combination of automatic processing based on user input (e.g., queries, data updates, etc.).

Memory 1422 may also store data used in performance of one or more aspects described herein, including a first database 1432 and a second database 1430. In some embodiments, the first database may include the second database (e.g., as a separate table, report, etc.). That is, the information can be stored in a single database, or separated into different logical, virtual, or physical databases, depending on system design. Web server 1406, computer 1404, laptop 1402 may have similar or different architecture as described with respect to data server 1410. Those of skill in the art will appreciate that the functionality of data server 1410 (or web server 1406, computer 1404, laptop 1402) as described herein may be spread across multiple data processing devices, for example, to distribute processing load across multiple computers, to segregate transactions based on geographic location, user access level, quality of service (QoS), etc.

One or more aspects may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a nonvolatile storage device. Any suitable computer readable storage media may be utilized, including hard disks, CD-ROMs, optical storage devices, magnetic storage devices, and/or any combination thereof. In addition, various transmission (non-storage) media representing data or events as described herein may be transferred between a source and a destination in the form of electromagnetic waves traveling through signal-conducting media such as metal wires, optical fibers, and/or wireless transmission media (e.g., air and/or space). various aspects described herein may be embodied as a method, a data processing system, or a computer program product. Therefore, various functionalities may be embodied in whole or in part in software, firmware and/or hardware or hardware equivalents such as integrated circuits, field programmable gate arrays (FPGA), and the like. Particular data structures may be used to more effectively implement one or more aspects described herein, and such data structures are contemplated within the scope of computer executable instructions and computer-usable data described herein.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A computer implemented method comprising:

receiving, by a processor, input data from a mass spectrometry apparatus, the input data representing a fragmentation of a molecule into a plurality of experimental fragments, where the input data comprises mass-to-charge ratios and intensity values for detected ions;

comparing, by the processor, the fragmentation to a library of modeled fragmentations to identify a candidate match comprising a plurality of modeled fragments, the comparing comprising:

selecting, by the processor, a model fragmentation pattern in the library of modeled fragmentations, calculating, using the processor, a coverage score for the selected model fragmentation pattern by determining a closeness of a match of at least one fragment corresponding to a first mass peak in the model fragmentation pattern to at least one fragment corresponding to a second mass peak in the plurality of modeled fragments, and selecting, with the processor, the selected model fragmentation pattern as the candidate match based on the coverage score; and displaying, via a graphical user interface, a graphical representation of the candidate match, the graphical representation comprising a graphical element corresponding to each of the modeled fragments, wherein each graphical element is capable of being in an on state or an off state, and a respective graphical element is in the on state if the graphical element's modeled fragment matches a corresponding experimental fragment in the input data based on the experimental fragment having a mass-to-charge ratio matching within a predetermined mass tolerance window of the modeled fragment and having an intensity value above a predetermined minimum threshold.

2. The computer-implemented method of claim 1, wherein the molecule is an oligonucleotide and the experimental fragments represent monomers in the oligonucleotide.

3. The computer-implemented method of claim 1, further comprising:

receiving second input data representing a second fragmentation of the molecule into a second plurality of experimental fragments; and aggregating at least the plurality of experimental fragments and the second plurality of experimental fragments into cumulative input data, wherein the respective graphical element is in the on state if the modeled fragment corresponding to the graphical element matches at least one of the corresponding experimental fragment in the input data or a second corresponding experimental fragment from the second input data.

4. The computer-implemented method of claim 3, wherein each graphical element displays a score representing how often the modeled fragment corresponding to the graphical element was found in the cumulative input data.

5. The computer-implemented method of claim 3, further comprising:

receiving a selection of a selected graphical element in the graphical representation of the candidate match; and highlighting corresponding graphical elements in graphical representations of the cumulative input data.

6. The computer-implemented method of claim 1, further comprising:

identifying a second candidate match; and displaying a graphical representation of the second candidate match aligned to a graphical representation of the candidate match.

7. The computer-implemented method of claim 1, further comprising:

identifying that a specified experimental fragment is associated with one or more variant configurations; and modifying the graphical element corresponding to the specified experimental fragment with a variant identifier.

8. The computer-implemented method of claim 7, further comprising:

identifying that a plurality of experimental fragments are each associated with one or more variant configurations, and that at least one of the experimental fragments is in a variant state; and modifying the graphical elements corresponding to the plurality of experimental fragments associated with the variant configurations with a potential variant identifier.

9. The computer-implemented method of claim 7, further comprising:

receiving a selection of the graphical element corresponding to the specified experimental fragment;

receiving a selection of a selected variant configuration; and modifying the display of the graphical representation based on the selected variant configuration.

10. The computer-implemented method of claim 1, further comprising:

receiving a selection of a selected graphical element in the graphical representation of the candidate match; and displaying a mass spectrum from the input data corresponding to the experimental fragment associated with the selected graphical element.

11. The method of claim 1, wherein the comparing comprises:

retrieving a hypothetical fragmentation for one of the modeled fragmentations in the library into constituent ions;

identifying, for each experimental fragment in the input data, an experimental mass peak;

identifying, for each constituent ion in the hypothetical fragmentation, a predicted mass-to-charge ratio value for the constituent ion;

establishing a predetermined window around the predicted mass-to-charge ratio value for the constituent ion; and determining that the constituent ion in the hypothetical fragmentation is a match for the experimental fragment in the input data when the experimental mass peak falls within the predetermined window.

12. A non-transitory computer-readable storage medium, the computer-readable storage medium including instructions that when executed by a computer, cause the computer to:

receive, using a processor, input data representing a fragmentation of a molecule into a plurality of experimental fragments, where the input data comprises mass-to-charge ratios and intensity values for detected ions;

compare, using the processor, the fragmentation to a library of modeled fragmentations to identify a candidate match comprising a plurality of modeled fragments, the comparing comprising:

selecting, by the processor, a model fragmentation pattern in the library of modeled fragmentations, calculating, using the processor, a coverage score for the selected model fragmentation pattern by determining a closeness of a match of at least one fragment corresponding to a first mass peak in the model fragmentation pattern to at least one fragment corresponding to a second mass peak in the plurality of modeled fragments, and selecting, with the processor, the selected model fragmentation pattern as the candidate match based on the coverage score; and display, via a graphical user interface, a graphical representation of the candidate match, the graphical representation comprising a graphical element corresponding to each of the modeled fragments, wherein each graphical element is capable of being in an on state or an off state, and a respective graphical element is in the on state if the graphical element's modeled fragment matches a corresponding experimental fragment in the input data based on the experimental fragment having a mass-to-charge ratio matching within a predetermined mass tolerance window of the modeled fragment and having an intensity value above a predetermined minimum threshold.

13. The computer-readable storage medium of claim 12, wherein the molecule is an oligonucleotide and the experimental fragments represent monomers in the oligonucleotide.

14. The computer-readable storage medium of claim 12, wherein the instructions further configure the computer to:

receive second input data representing a second fragmentation of the molecule into a second plurality of experimental fragments; and aggregate at least the plurality of experimental fragments and the second plurality of experimental fragments into cumulative input data, wherein the respective graphical element is in the on state if the modeled fragment corresponding to the graphical element matches at least one of the corresponding experimental fragment in the input data or a second corresponding experimental fragment from the second input data.

15. The computer-readable storage medium of claim 14, wherein each graphical element displays a score represent how often the modeled fragment corresponding to the graphical element was found in the cumulative input data.

16. The computer-readable storage medium of claim 14, wherein the instructions further configure the computer to:

receive a selection of a selected graphical element in the graphical representation of the candidate match; and highlight corresponding graphical elements in graphical representations of the cumulative input data.

17. The computer-readable storage medium of claim 12, wherein the instructions further configure the computer to:

identify a second candidate match; and display a graphical representation of the second candidate match aligned to a graphical representation of the candidate match.

18. The computer-readable storage medium of claim 12, wherein the instructions further configure the computer to:

identify that a specified experimental fragment is associated with one or more variant configurations; and modify the graphical element corresponding to the specified experimental fragment with a variant identifier.

19. The computer-readable storage medium of claim 18, wherein the instructions further configure the computer to:

identify that a plurality of experimental fragments are each associated with one or more variant configurations, and that at least one of the experimental fragments is in a variant state; and modify the graphical elements corresponding to the plurality of experimental fragments associated with the variant configurations with a potential variant identifier.

20. The computer-readable storage medium of claim 18, wherein the instructions further configure the computer to:

receive a selection of the graphical element corresponding to the specified experimental fragment;

receive a selection of a selected variant configuration; and modify the display of the graphical representation based on the selected variant configuration.

21. The computer-readable storage medium of claim 12, wherein the instructions further configure the computer to:

receive a selection of a selected graphical element in the graphical representation of the candidate match; and display a mass spectrum from the input data corresponding to the experimental fragment associated with the selected graphical element.

* * * * *